(12) United States Patent
Johnson et al.

(10) Patent No.: US 8,021,873 B2
(45) Date of Patent: Sep. 20, 2011

(54) PORTABLE, POINT-OF-CARE, USER-INITIATED FLUIDIC ASSAY METHODS AND SYSTEMS

(75) Inventors: Brandon T. Johnson, Cambridge, MA (US); Tom Zappia, Somerville, MA (US); David A. Vogler, Rochester, NY (US)

(73) Assignee: Boston Microfluidics, Cambridge, MA (US)

(*) Notice: Subject to any disclaimer, the term of this patent is extended or adjusted under 35 U.S.C. 154(b) by 244 days.

(21) Appl. No.: 12/228,081

(22) Filed: Jul. 16, 2008

(65) Prior Publication Data
US 2010/0015646 A1    Jan. 21, 2010

(51) Int. Cl.
*C12M 1/34* (2006.01)
(52) U.S. Cl. ............... 435/288.5; 435/283.1; 435/287.1; 427/2.11; 427/8
(58) Field of Classification Search ............ None
See application file for complete search history.

(56) References Cited

U.S. PATENT DOCUMENTS

| | | | |
|---|---|---|---|
| 3,579,306 A | 5/1971 | Crane |
| 3,684,455 A | 8/1972 | Vacirca et al. |
| 3,733,179 A | 5/1973 | Guehler |
| 3,986,834 A | 10/1976 | Steinbrink, Jr. |
| 4,162,003 A | 7/1979 | Bartos et al. |
| 4,277,560 A | 7/1981 | Gray et al. |
| 4,308,347 A | 12/1981 | Forrer et al. |
| 4,515,753 A | 5/1985 | Smith et al. |
| 4,580,682 A | 4/1986 | Gorski et al. |
| 4,582,685 A | 4/1986 | Guadagno et al. |
| 4,637,061 A | 1/1987 | Riese |
| 4,729,875 A | 3/1988 | Chandler |
| 4,732,850 A | 3/1988 | Brown et al. |
| 5,024,238 A | 6/1991 | Guirguis |

(Continued)

OTHER PUBLICATIONS

International Search report and Written Opinion for PCT Application No. PCT/US2009/50775, mailed on Aug. 31, 2009, 15 pages.

(Continued)

*Primary Examiner* — Nelson C. Yang
(74) *Attorney, Agent, or Firm* — Garrett IP, LLC

(57) ABSTRACT

Methods and systems to perform point-of-care, user-initiated fluidic assays, using substantially self-contained, portable, user-initiated fluidic assay systems. Exemplary assays include diagnostic assays and chemical detection assays. Diagnostic assays may include, without limitation, enzyme-linked immuno-sorbent assays (ELISA), and may include one or more sexually transmitted disease (STD) diagnostic assays. An exemplary assay system includes a housing having one or more fluid chambers, a fluid controller system to dispense fluid from the one or more fluid chambers, and a user-initiated actuator to control the fluid controller system. The actuator may be configured to move fluid controllers from functionally closed positions to functionally open positions, to control fluid flow from the fluid chambers. The fluid controller system may be configured to dispense fluids serially, and may be configured to mix a plurality of fluids. The housing may include one or more fluid paths amongst the fluid chambers and/or between the fluid chambers and an assay portion, and the fluid controller system may be configured to serially align fluid chamber outlets with corresponding fluid paths. The user-initiated actuator system may include an external user-operated trigger mechanism to initiate the actuator system. The actuator system may include a mechanical actuator system, and may include a compressible spring actuator system. The assay apparatus may include a display window to view assay results. Exemplary methods of preparing portable, user-initiated fluidic assay systems, and methods of using portable, user-initiated fluidic assay systems are disclosed.

18 Claims, 33 Drawing Sheets

U.S. PATENT DOCUMENTS

| | | | |
|---|---|---|---|
| 5,143,084 A * | 9/1992 | Macemon et al. | 600/584 |
| 5,152,965 A | 10/1992 | Fisk et al. | |
| 5,183,740 A | 2/1993 | Ligler et al. | |
| 5,270,069 A | 12/1993 | Plester | |
| 5,391,478 A | 2/1995 | Greene et al. | |
| 5,415,994 A | 5/1995 | Imrich et al. | |
| 5,418,167 A | 5/1995 | Matner et al. | |
| 5,516,638 A | 5/1996 | Urnovitz et al. | |
| 5,552,320 A | 9/1996 | Smith | |
| 5,704,501 A | 1/1998 | Valyi | |
| 5,731,162 A | 3/1998 | Gatti et al. | |
| 5,750,184 A | 5/1998 | Imburgia | |
| 5,817,522 A | 10/1998 | Goodman et al. | |
| 5,824,268 A | 10/1998 | Bernstein et al. | |
| 5,866,356 A | 2/1999 | Albert et al. | |
| 6,077,660 A | 6/2000 | Wong et al. | |
| 6,079,871 A | 6/2000 | Jonas et al. | |
| 6,120,733 A * | 9/2000 | Goodman et al. | 422/61 |
| 6,300,140 B1 | 10/2001 | Robinson et al. | |
| 6,300,142 B1 | 10/2001 | Andrewes et al. | |
| 6,312,888 B1 | 11/2001 | Wong et al. | |
| 6,488,894 B1 * | 12/2002 | Miethe et al. | 422/100 |
| 6,503,702 B1 | 1/2003 | Stewart | |
| 6,623,955 B2 | 9/2003 | Matner et al. | |
| 6,737,278 B1 | 5/2004 | Carlsson et al. | |
| 6,827,899 B2 | 12/2004 | Maisey et al. | |
| 6,833,111 B2 | 12/2004 | Robertson et al. | |
| 6,893,816 B1 | 5/2005 | Beattie | |
| 7,018,830 B2 | 3/2006 | Wilding et al. | |
| 7,090,802 B1 | 8/2006 | Wang et al. | |
| 7,100,639 B2 | 9/2006 | Rub | |
| 7,132,078 B2 | 11/2006 | Rawson et al. | |
| 7,157,234 B2 | 1/2007 | Obremski et al. | |
| 7,238,322 B2 | 7/2007 | Wang et al. | |
| 7,270,970 B2 | 9/2007 | Anderson et al. | |
| 7,303,925 B2 | 12/2007 | Sidewell et al. | |
| 7,311,195 B2 | 12/2007 | Schmid | |
| 7,358,079 B2 | 4/2008 | Schürmann-Mader et al. | |
| 7,381,375 B2 | 6/2008 | Ravkin et al. | |
| 7,517,495 B2 | 4/2009 | Wu et al. | |
| 7,531,362 B2 | 5/2009 | Chan | |
| 2003/0049857 A1 | 3/2003 | Chan | |
| 2004/0031488 A1 * | 2/2004 | Terada et al. | 128/203.15 |
| 2007/0299390 A1 | 12/2007 | Bellhouse et al. | |
| 2008/0041738 A1 | 2/2008 | O'Donnell et al. | |
| 2009/0123336 A1 | 5/2009 | Yang et al. | |
| 2009/0176316 A1 | 7/2009 | Giter et al. | |
| 2009/0215159 A1 | 8/2009 | Kirby | |
| 2009/0215194 A1 | 8/2009 | Magni et al. | |

OTHER PUBLICATIONS

International Search Report for International Application No. PCT/US10/53444 mailed on Feb. 23, 2011, 4 pages.

* cited by examiner (Serial Dispensing)

(Serial Dispensing)

(Serial Mixing)

(Serial Mixing)

(Serial Mixing)

(Serial Mixing)

(Simultaneous Mixing)

(Simultaneous Mixing)

(Simultaneous Mixing)

(Simultaneous Mixing, Opposing Directions)

(Simultaneous Mixing, Opposing Directions)

(Simultaneous Mixing, Opposing Directions)

PORTABLE, POINT-OF-CARE, USER-INITIATED FLUIDIC ASSAY METHODS AND SYSTEMS

BACKGROUND

Given the great strain on the healthcare work force, the increased prevalence of many common diseases and the substantial delay in treatment caused by remote testing, it has become imperative to develop rapid, easy-to-use automated diagnostic devices and platforms to enable efficient and accurate point-of-care disease detection.

Historic obstacles to point-of-care devices include manufacturing challenges, ease-of-use limitations, and government regulations. Some of these obstacles have been reduced through advances in technology and recognition by governments and other regulatory bodies of the importance of point-of-care testing. However, important considerations, including ease-of-use and accuracy, still render point-of-care tests unsuitable for many healthcare facilities.

Conventional point-of-care diagnostic systems utilize capillary action or test strips, which provide limited ability to perform many diagnostic assays, such as fluidic assays.

Fluidic assays, such as enzyme-linked immuno-sorbent assays (ELISAs), are capable of detecting the presence of many diseases ranging from cancer to diseases like herpes simplex type 2, and generally require relatively few operational steps. However, these steps are typically preformed by trained lab technicians.

SUMMARY

Disclosed herein are methods and systems to perform point-of-care, user-initiated fluidic assays, using substantially self-contained, portable, user-initiated fluidic assay systems.

Exemplary assays include diagnostic assays and chemical detection assays. Diagnostic assays include, without limitation, enzyme-linked immuno-sorbent assays (ELISA), and may include one or more sexually transmitted disease (STD) diagnostic assays.

An exemplary assay system includes a housing having one or more fluid chambers, a fluid controller system to dispense fluid from the one or more fluid chambers, and a user-initiated actuator to control the fluid controller system.

The actuator may be configured to serially move fluid controllers from functionally closed positions to functionally open positions, to control fluid flow from the fluid chambers.

The fluid controller system may be configured to dispense fluids serially, and may be configured to mix a plurality of fluids.

The housing may include an assay portion and the fluid controller system may be configured to dispense fluids from one or more of the fluid chambers to the assay portion.

The housing may include one or more fluid paths amongst the fluid chambers and/or to the assay portion, and the fluid controller system may be configured to serially align fluid chamber outlets with corresponding fluid paths.

The housing may include a sample chamber to receive an assay sample, such as a biological sample, and one or more of the fluid paths may include the sample chamber.

The user-initiated actuator system may include an external user-operated trigger mechanism to initiate the actuator system. The actuator system may include a mechanical actuator system, and may include a compressible spring actuator system.

The assay apparatus may include a display window to view assay results.

BRIEF DESCRIPTION OF THE DRAWINGS/FIGURES

In the drawings, like reference numbers indicate identical or functionally similar elements. Additionally, the leftmost digit(s) of a reference number identifies the drawing in which the reference number first appears.

DETAILED DESCRIPTION

Figure 1:
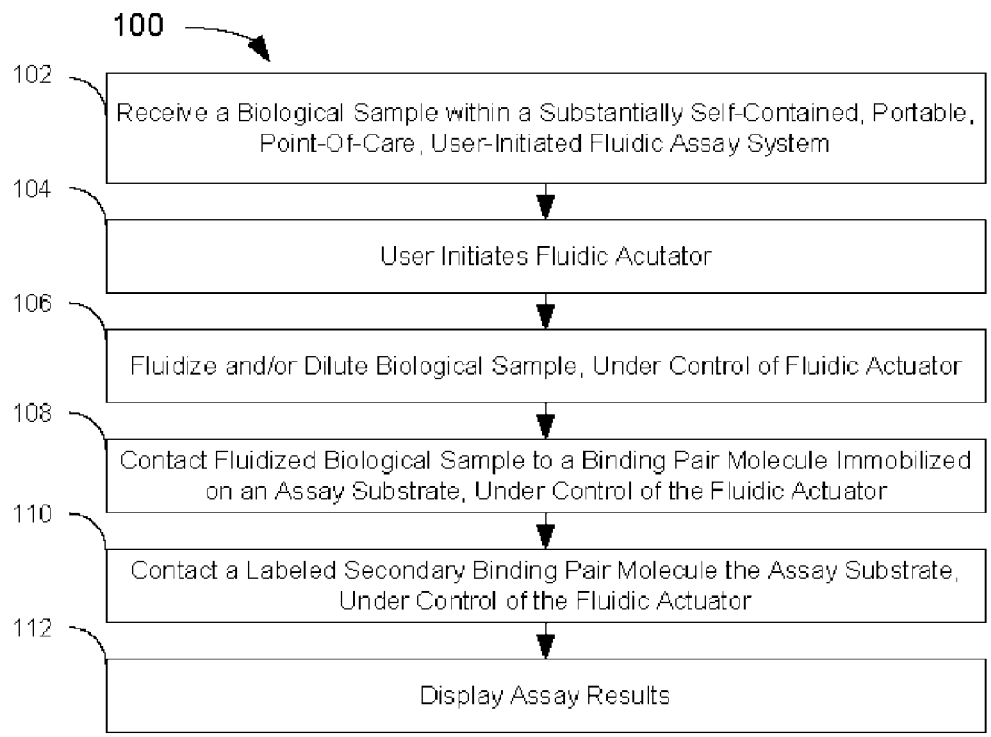
FIG. 1 is a process flowchart of an exemplary method of performing an assay with a substantially self-contained, point-of-care, user-initiated fluidic assay system.

Disclosed herein are methods of performing point-of-care, user-initiated fluidic assays, and substantially self-contained, portable, point-of-care, user-initiated fluidic assay systems.

Exemplary methods and systems are described herein with respect to immunoassays, for illustrative purposes. Based on the teachings herein, one skilled in the art will understand that the methods may be implemented with respect to other diagnostic assays and with respect to chemical assays.

An immunoassay is a biochemical test to detect a substance, or measure a concentration of a substance, in a biological sample such as blood, saliva, or urine, using a reaction between an antibody and an antigen specific to the antibody.

An immunoassay may be used to detect the presence of an antigen or an antibody. For example, when detecting an infection, the presence of an antibody against the pathogen may be measured. When detecting hormones such as insulin, the insulin may be used as the antigen.

Accordingly, where a method or system is described herein to detect a primary binding pair molecule using a corresponding second binding pair molecule, it should be understood that the primary binding pair molecule may be an antibody or an antigen, and the second binding pair molecule may be a corresponding antigen or antibody, respectively. Similarly, where a method or system is described herein to detect an antibody or antigen, the method or system may be implemented to detect a corresponding antigen or antibody, respectively.

Immunoassays may also be used to detect potential food allergens and chemicals, or drugs.

Immunoassays include labeled immunoassays to provide a visual indication of a binding pair of molecules. Labeling may include an enzyme, radioisotopes, magnetic labels, fluorescence, agglutination, nephelometry, turbidimetry and western blot.

Labeled immunoassays include competitive and non-competitive immunoassays. In a competitive immunoassay, an antigen in a sample competes with labeled antigen to bind with antibodies. The amount of labeled antigen bound to the antibody site is inversely proportional to the concentration of antigen in the sample. In noncompetitive immunoassays, also referred to as sandwich assays, antigen in a sample is bound to an antibody site. The labeled antibody is then bound to the antigen. The amount of labeled antibody on the site is directly proportional to the concentration of the antigen in the sample.

Labeled immunoassays include enzyme-linked immunosorbent assays (ELISA).

In an exemplary immunoassay, a biological sample is tested for a presence of a primary binding pair molecule. A corresponding binding pair molecule that is specific to the primary binding pair molecule is immobilized on an assay substrate. The biological sample is contacted to the assay substrate. Any primary binding pair molecules in the biological sample attach to, or are captured by the corresponding binding pair molecules. The primary binding pair molecules are also contacted with labeled secondary binding pair molecules that attach to the primary binding pair molecules. This may be performed subsequent to, prior to, or simultaneously with the contacting of the primary binding pair molecule with the corresponding immobilized binding pair molecule. Unreacted components of the biological sample and fluids may be removed, or washed from the assay substrate. Presence of the label on the assay substrate indicates the presence of the primary binding pair molecule in the biological sample.

The label may include a directly detectable label, which may be visible to a human observer, such as gold particles in a colloid or solution, commonly referred to as colloidal gold.

The label may include an indirect label, such an enzyme whereby the enzyme works on a substrate to produce a detectable reaction product. For example, an enzyme may attach to the primary binding pair molecule, and a substance that the enzyme converts to a detectable signal, such as a fluorescence signal, is contacted to the assay substrate. When light is directed at the assay substrate, any binding pair molecule complexes will fluoresce so that the presence of the primary binding pair molecule is observable.

An immunoassay may utilize one or more fluid solutions, which may include a dilutent solution to fluidize the biological sample, a conjugate solution having the labeled secondary binding pair molecules, and one or more wash solutions. The biological sample and fluids may be brought into contact, concurrently or sequentially with the assay substrate. The assay substrate may include an assay surface or an assay membrane, prepared with a coating of the corresponding binding pair molecules.

As described above, the second binding pair molecules may include an antigen that is specific to an antibody to be detected in a biological sample, or may include antibody that is specific to an antigen to be detected in the biological sample. By way of illustration, if the primary binding pair molecule to be detected is an antigen, the immobilized binding pair molecule and the secondary labeled binding pair molecule will be antibodies, both of which react with the antigen. When the antigen is present in the biological sample, the antigen will be immobilized by the immobilized antibody and labeled by the labeled secondary antibody, to form a sandwich-like construction, or complex.

It is known that non-specific or un-reacted components may be beneficially removed using wash solutions, often between processes and/or prior to a label detection process, in order to improve sensitivity and signal-to-noise ratios of the assay. Other permutations are possible as well. For example, a conjugate solution, such as a labeled secondary binding pair molecule solution may be mixed with or act as a sample dilutent to advantageously transport the biological sample to the assay substrate, to permit simultaneous binding of the primary binding pair molecule and the labeled secondary binding pair molecule to the immobilized binding pair molecule. Alternatively, or additionally, the sample dilutent may include one or more detergents and/or lysing agents to advantageously reduce deleterious effects of other components of the biological sample such as cellular membranes, non-useful cells like erythrocytes and the like.

Those skilled in the art will readily recognize that such fluid components and the order of the reactionary steps may be readily adjusted along with concentrations of the respective components in order to optimize detection or distinguishment of analytes, increase sensitivity, reduce non-specific reactions, and improve signal to noise ratios.

As will be readily understood, if the secondary antibody is labeled with an enzyme instead of a fluorescent or other immediately detectable label, an additional substrate may be utilized to allow the enzyme to produce a reaction product which will be advantageously detectable. An advantage of using an enzyme based label is that the detectable signal may increase over time as the enzyme works on an excess of substrate to produce a detectable product.

FIG. 1 is a process flowchart of an exemplary method 100 of detecting a primary binding pair molecule in a biological sample, using a substantially self-contained, point-of-care, user-initiated fluidic assay system. The primary binding pair molecule may correspond to an antibody or an antigen.

At 102, a biological sample is provided to the assay system. The biological sample may include one or more of a blood sample, a saliva sample, and a urine sample. The biological sample may be applied to a sample substrate within the assay system.

At 104, a fluidic actuator within the assay system is initiated by a user. The fluidic actuator may include a mechanical actuator, such as a compressed spring actuator, and may be initiated with a button, switch, or lever. The fluidic actuator may be configured to impart one or more of a physical force, pressure, centripetal force, gas pressure, gravitational force, and combinations thereof, on a fluid controller system within the assay system.

At 106, the biological sample is fluidized with a dilutent fluid. The dilutent fluid may flow over or through the sample substrate, under control of the fluid controller system.

At 108, the fluidized biological sample is contacted to a corresponding binding pair molecule that is specific to primary binding pair molecule. The corresponding binding pair molecule may be immobilized on an assay substrate within the assay system. The fluidized biological sample may flow over or through the assay substrate, under control of the fluid controller system.

Where the fluidized biological sample includes the primary binding pair molecule, the primary binding pair molecule attaches to the corresponding binding pair molecule and becomes immobilized on the assay substrate. For example, where the second binding pair molecule includes a portion of a pathogen, and where the biological sample includes an antibody to the pathogen, the antibody attaches to the antigen immobilized at the assay substrate.

At 110, a labeled conjugate solution is contacted to the assay substrate, under control of the fluid controller system. The labeled conjugate solution includes a secondary binding pair molecule to bind with the primary binding pair molecule. Where the primary binding pair molecule is immobilized on the assay substrate with the corresponding binding pair molecule, the secondary binding pair molecule attaches to the immobilized primary binding pair molecule, effectively creating a sandwich-like construct of the primary binding pair molecule, the corresponding binding pair molecule, and the labeled secondary binding pair molecule.

The secondary binding pair molecule may be selected as one that targets one or more proteins commonly found in the biological sample. For example, where the biological sample includes a human blood sample, the secondary binding pair molecule may include an antibody generated by a non-human animal in response to the one or more proteins commonly found in human blood.

The secondary binding pair molecule may be labeled with human-visible particles, such as a gold colloid, or suspension of gold particles in a fluid such as water. Alternatively, or additionally, the secondary binding pair molecule may be labeled with a fluorescent probe.

Where the labeled secondary binding pair molecule attaches to a primary binding pair molecule that is attached to a corresponding binding pair molecule, at 110, the label is viewable by the user at 112.

Figure 2:
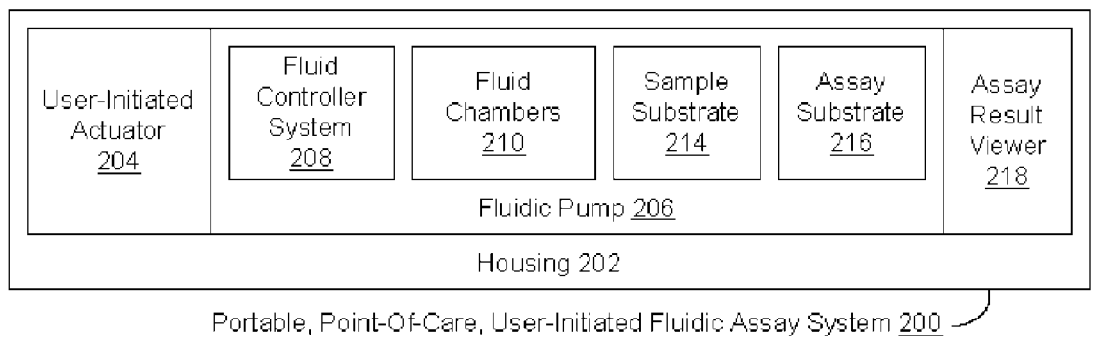
FIG. 2 is a block diagram of an exemplary portable, point-of-care, user-initiated fluidic assay system.

Method 100 may be implemented to perform multiple diagnostic assays in an assay system. For example, a plurality of antigens, each specific to a different antibody, may be immobilized on one or more assay substrates within an assay system. Similarly, a plurality of antibodies, each specific to a different antigen, may be immobilized on one or more assay substrates within an assay system FIG. 2 is a block diagram of an exemplary portable, point-of-care, user-initiated fluidic assay system 200, including a housing 202, a user-initiated actuator 204, a fluidic pump 206, and an assay result viewer 218.

Pump 206 includes one or more fluid chambers 210, to contain fluids to be used in an assay. One or more of fluid chambers 210 may have, without limitation, a volume in a range of 0.5 to 2 milliliters.

Pump 206 includes a sample substrate 214 to hold a sample. Sample substrate 214 may include a surface or a membrane positioned within a cavity or a chamber of housing 202, to receive one or more samples, as described above.

Sample substrate 214 may include a porous and/or absorptive material, which may be configured to absorb a volume of liquid in a range of 10 to 500 μL, including within a range of up to 200 μL, and including a range of approximately 25 to 50 μL.

Pump 206 includes an assay substrate 216 to hold an assay material. Assay substrate 216 may include a surface or a membrane positioned within a cavity or chamber of housing 202, to receive one or more assay compounds or biological components, such as an antigen or an antibody, as described above.

Fluid chambers 210 may include a waste fluid chamber.

Pump 206 further includes a fluid controller system 208, which may include a plurality of fluid controllers, to control fluid flow from one or more fluid chambers 212 to one or more of sample substrate 214 and assay substrate 216, responsive to actuator 204.

Actuator 204 may include a mechanical actuator, which may include a compressed or compressible spring actuator, and may include a button, switch, lever, twist-activator, or other user-initiated feature.

Assay result viewer 218 may include a display window disposed over an opening through housing 202, over assay substrate 216.

Figure 3:
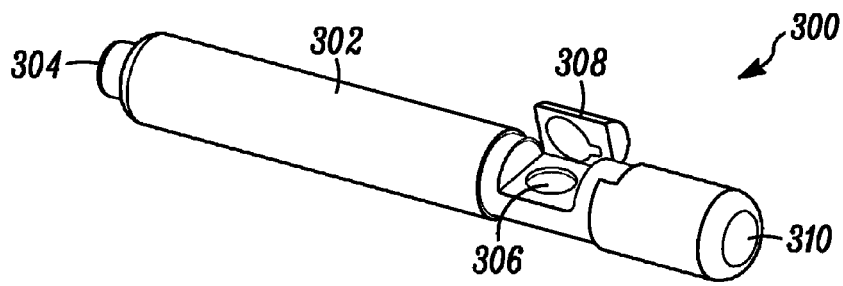
FIG. 3 is a perspective view of an exemplary portable, point-of-care, user-initiated fluidic assay system.

FIG. 3 is a perspective view of an exemplary portable, point-of-care, user-initiated fluidic assay system 300, including a housing 302, a user-initiated actuator button 304, a sample substrate 306, and a sample substrate cover 308.

Sample substrate cover 308 may be hingedly coupled to housing 302.

Assay system 300 further includes an assay result viewer 310, which may be disposed over an assay substrate. Assay result view 310 may be disposed at an end of assay system 300, as illustrated in FIG. 3, or along a side of assay system 300.

Assay system 300 may have, without limitation, a length in a range of 5 to 8 centimeters and a width of approximately 1 centimeter. Assay system 300 may have a substantially cylindrical shape, as illustrated in FIG. 3, or other shape.

Assay system 300, or portions thereof, may be implemented with one or more substantially rigid materials, and/or with one or more flexible or pliable materials, including, without limitation, polypropylene.

Exemplary portable, point-of-care, user-initiated fluidic assay systems are disclosed further below.

Figure 4:
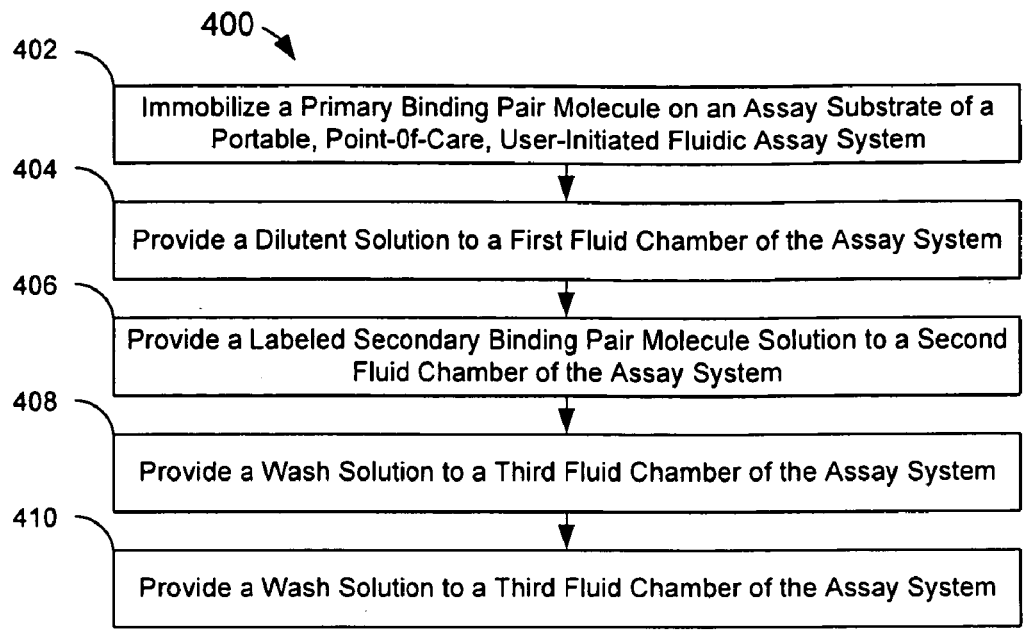
FIG. 4 is a process flowchart of an exemplary method of preparing a portable, point-of-care, user-initiated fluidic assay system.

FIG. 4 is a process flowchart of an exemplary method 400 of preparing a portable, point-of-care, user-initiated fluidic assay system. Method 400 is described below with reference to assay system 200 in FIG. 2, for illustrative purposes. Method 400 is not, however, limited to the example of FIG. 2.

At 402, a binding pair molecule is immobilized on an assay substrate, such as assay substrate 216 in FIG. 2. The binding pair molecule may include an antigen specific to an antibody, or an antibody specific to an antigen.

At 404, a first one of fluid chambers 210 is provided with a dilutent solution to fluidize a sample.

At 406, a second one of fluid chambers 210 is provided with a labeled secondary binding pair molecule solution.

At 408, a third one of fluid chambers 210 is provided with a wash solution, which may include one or more of a saline solution and a detergent. The wash solution may be substantially similar to the dilutent solution.

Figure 5:
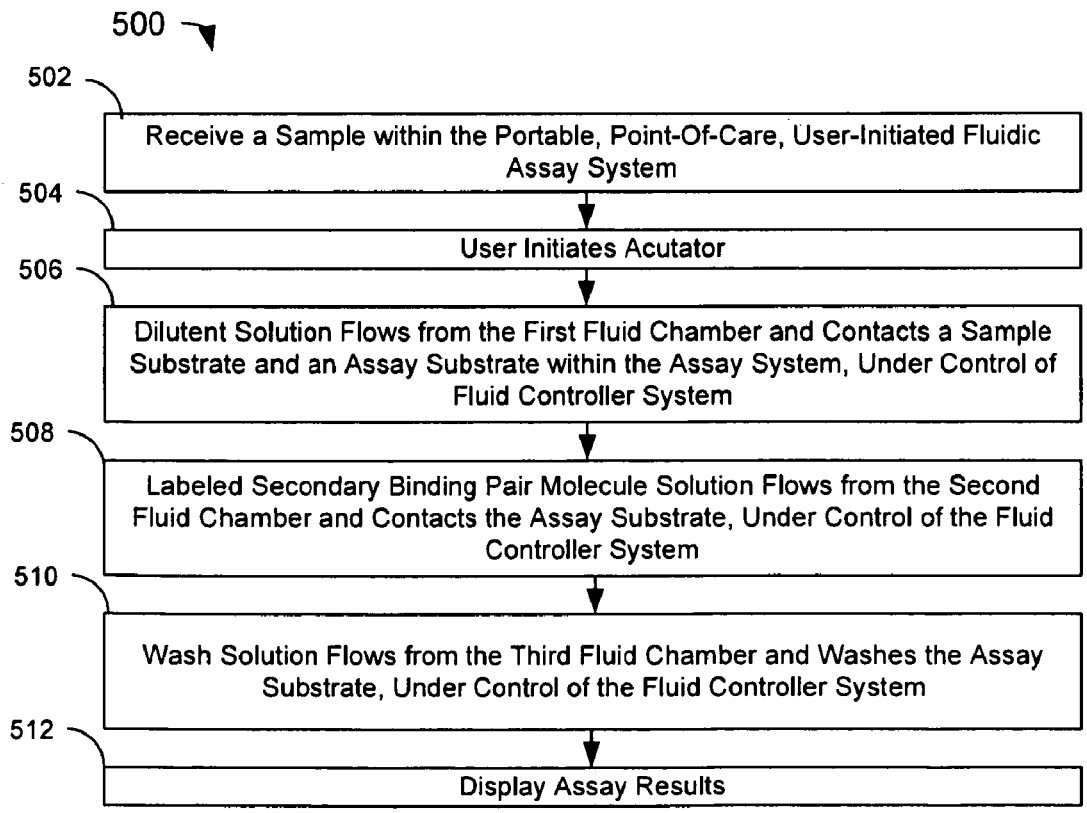
FIG. 5 is a process flowchart of an exemplary method of using an assay system prepared in accordance with FIG. 4.

FIG. 5 is a process flowchart of an exemplary method 500 of using an assay system prepared in accordance with method 400. Method 500 is described below with reference to assay system 200 in FIG. 2, and assay system 300 in FIG. 3, for illustrative purposes. Method 500 is not, however, limited to the examples of FIG. 2 and FIG. 3.

At 502, a sample is provided to a sample substrate, such as sample substrate 214 in FIG. 2, and sample substrate 306 in FIG. 3.

At 504, a user-initiated actuator is initiated by the user, such as user-initiated activator 204 in FIG. 2, and button 304 in FIG. 3. The user initiated actuator acts upon a fluid controller system, such as fluid controller system 208 in FIG. 2.

At 506, the dilutent solution flows from first fluid chamber and contacts the sample substrate and the assay substrate, under control of the fluid controller system.

As the dilutent fluid flows over or through the sample substrate, the sample is dislodged from the sample substrate and flows with the dilutent solution to the assay substrate.

At 508, the labeled secondary binding pair solution flows from the second fluid chamber and contacts the assay substrate, under control of the fluid controller system. The labeled secondary binding pair solution may flow directly to the assay substrate or may flow over or through the sample substrate.

At 510, the wash solution flows from the third fluid chamber and washes the assay substrate, under control of fluid controller system 208. The wash solution may flow from the assay substrate to a waste fluid chamber, At 512, assay results are viewable, such as at assay result viewer 218 in FIG. 2, and assay result viewer 310 in FIG. 3.

An exemplary assay substrate may include a nitrocellulose-based membrane, available from Invitrogen Corporatation, of Carlsbad, Calif.

Exemplary preparation of a nitrocellulose-based membrane may include incubation for approximately thirty (30) minutes in a solution of 0.2 mg/mL protein A, available from Sigma-Aldrich Corporation, of St. Louis, Mo., in a phosphate buffered saline solution (PBS), and then dried at approximately 37° for approximately fifteen (15) minutes. 1 µL of PBS may be added to the dry membrane and allowed to dry at room temperature. Alternatively, 1 µL of an N-Hydroxysuccinimide (NHS) solution, available from Sigma-Aldrich Corporation, of St. Louis, Mo., may be added to the dry membrane and allowed to dry at room temperature.

An exemplary assay method and/or system may utilize or include approximately 100 µL of PBS/0.05% Tween wash buffer, available from Sigma-Aldrich Corporation, of St. Louis, Mo., and may utilize or include approximately 100 µL of protein G colloidal gold, available from Pierce Corporation, of Rockland, Ill.

An exemplary assay method and/or system may be configured to test for Chlamydia, and may utilize or include a sample membrane treated with wheat germ agglutinin, to which an approximately 50 µL blood sample is applied. Approximately 150 µL of a lysing solution may then be passed through the sample membrane and then contacted to an assay substrate. Thereafter, approximately 100 µL of a colloidal gold solution may be contacted to the assay substrate. Thereafter, approximately 500 µL of a wash solution, which may include the lysing solution, may be contacted to the assay membrane without passing through the sample membrane.

Additional exemplary features and embodiments are disclosed below. Based on the description herein, one skilled in the relevant art(s) will understand that exemplary features and embodiments described herein may be practiced in various combinations with one another.

1. Exemplary Multiple Fluid Chamber, Serial Fluid Pump

Figure 6:
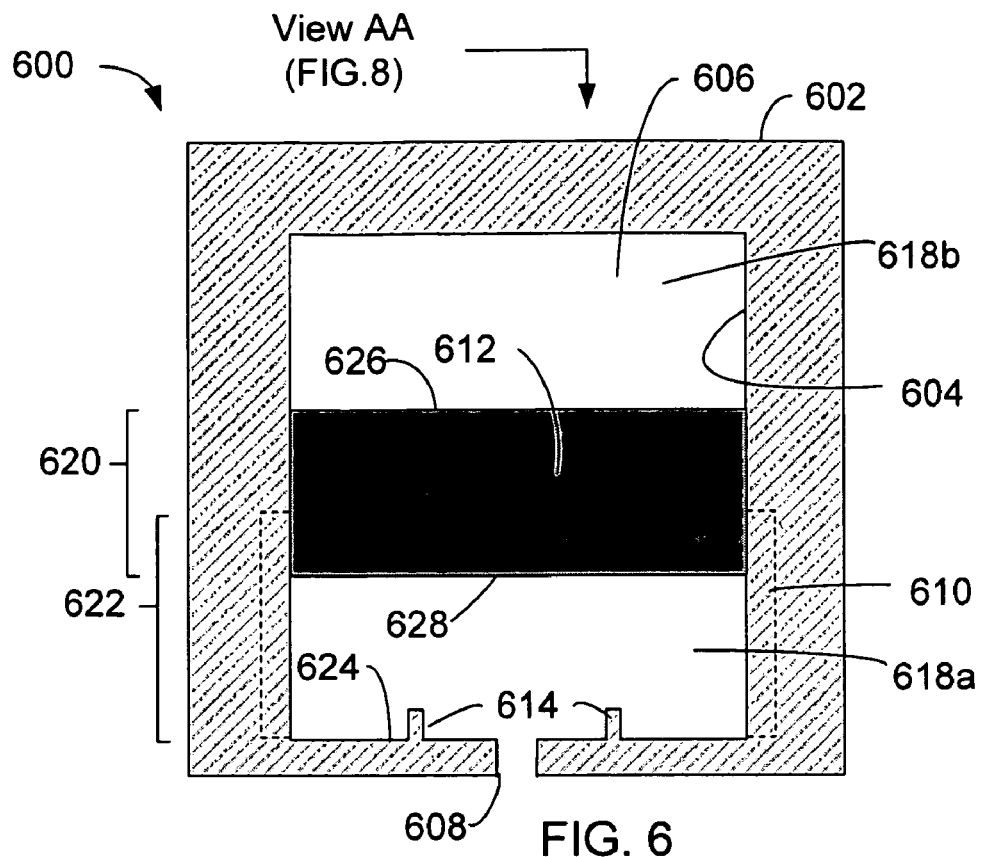
FIG. 6 is a cross-sectional block diagram of a pump 600.
Figure 7:
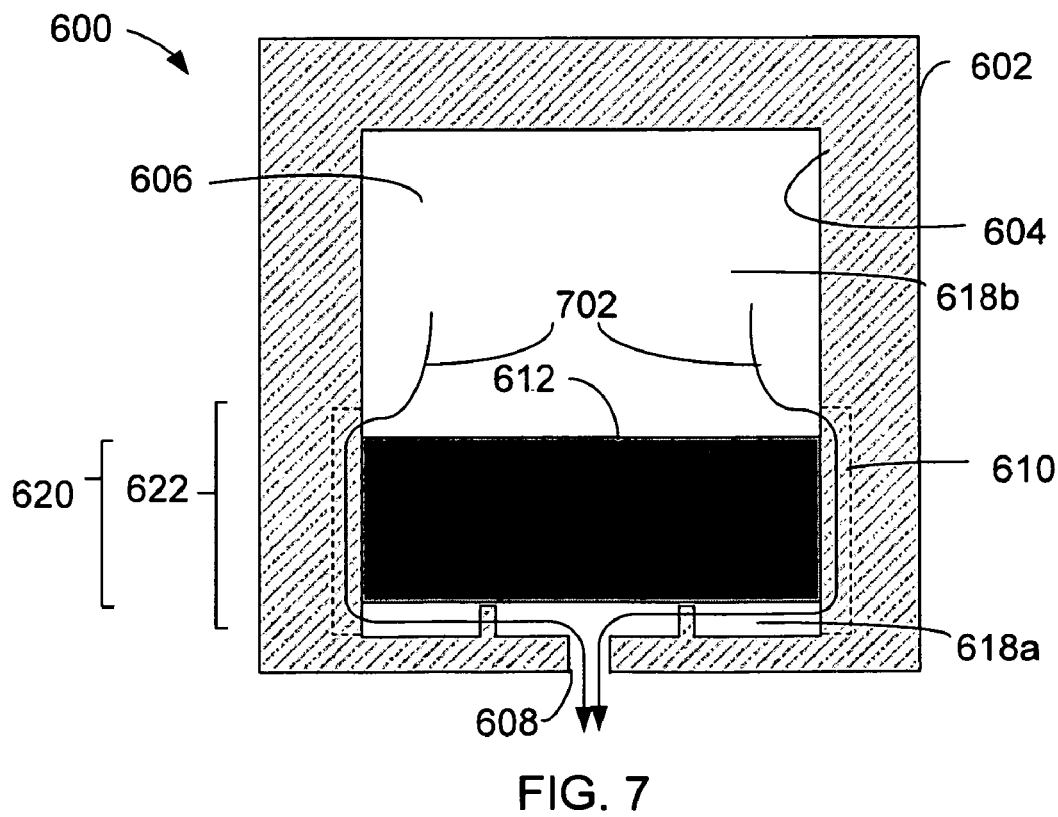
FIG. 7 is another cross-sectional block diagram of pump 600.

FIGS. 6 and 7 are cross-sectional block diagrams of an exemplary pump 600, including a housing 602 having an inner wall surface 604, defining a cavity 606 therein.

A fluid flow controller or plunger 612 is disposed within housing 602. Plunger 612 separates or defines first and second fluid chambers 618a and 618b. Plunger 612 is movable between a first position, as illustrated in FIG. 6, and a second position, as illustrated in FIG. 7. An outlet 608 in a base 624 of the housing 602 is in communication with second fluid chamber 618a. Plunger 612 is controllable to dispense fluid from fluid chamber 618a through outlet 608. Outlet 608 may lead to one or more other fluid chambers, which may include one or more of a sample substrate and an assay substrate.

Figure 8:
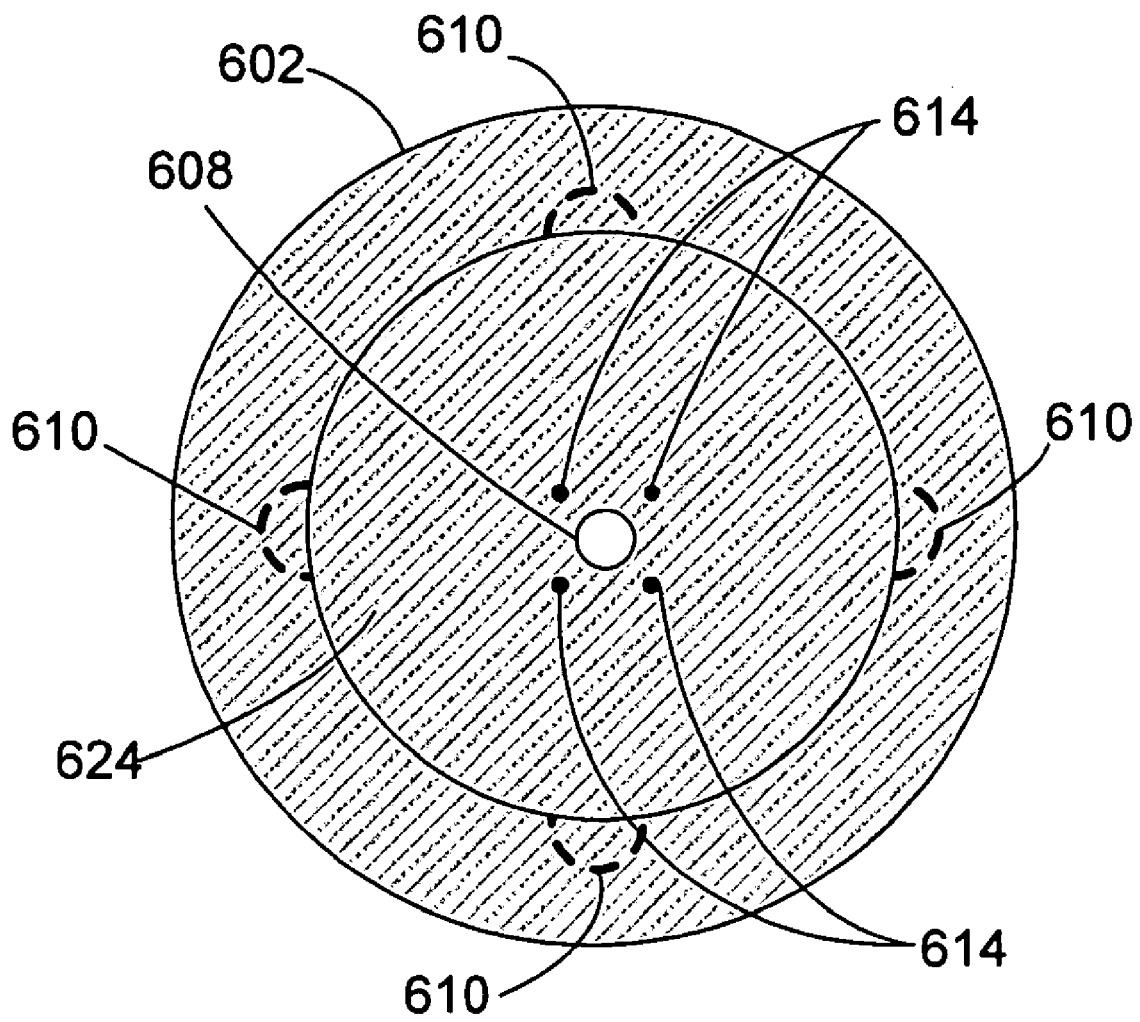
FIG. 8 is a cross-sectional block diagram of view A-A of pump 600.

A stop 614 prevents plunger 612 from obstructing or sealing outlet 608 when plunger 612 is in the second position (FIG. 7). Stop 614 can be implemented in a variety of ways. FIG. 8 is an exemplary cross-sectional view of housing 602, above base 624 according to view AA (FIG. 7), wherein stop 614 includes one or more protrusions extending from base 624 into cavity 606. Alternatively, stop 614 can include one or more protrusions extending from housing inner wall surface 604 into cavity 606, and/or extending from a surface 628 of plunger 612.

As illustrated in FIG. 7, when plunger 612 is in the second position, second fluid chamber 618b is in fluid communication with first fluid chamber 618a through a passageway or gate 610. The second position is referred to herein as a functionally open position.

Gate 610 may be formed, etched, engraved, carved, or otherwise implemented or imparted as one or more channels on surface 604 and/or as one or more passages within housing inner wall 604, wherein openings through housing inner wall surface 604 expose the one or more passages to the cavity 606.

Gate 610 and plunger 612 are configured and/or dimensioned so that plunger 612 obstructs, blocks, and/or seals gate 610, or a portion thereof, from second fluid chamber 618b when plunger 612 is in the first position, thereby isolating first fluid chamber 618a from second fluid chamber 118b, as illustrated in FIG. 6. The first position is referred to herein as a functionally closed position.

In the example of FIGS. 6 and 7, gate 610 has a length 622 that is dimensionally greater than a plunger edge height 620. In the functionally closed position, plunger 612 blocks at least a portion of gate 610, as illustrated in FIG. 6, or is positioned more distant from base 624, so that first fluid chamber 618a is isolated from second fluid chamber 118b.

Plunger 612 can be solid or hollow. Plunger surfaces 626 and 628 can be substantially flat, concave, convex, and/or combinations thereof.

Plunger 612 is controllable by, for example and without limitation, centripetal force, gas pressure, physical pressure, including manual activation, gravitational force, or combinations thereof.

In operation, as plunger 612 moves from the non-depressed or functionally closed position of FIG. 6, to the depressed or functionally open position of FIG. 7, fluid within first fluid chamber 618a is expelled through outlet 608. When plunger 612 reaches the depressed or functionally open position of FIG. 7, first fluid chamber 618a is in fluid communication with second fluid chamber 618b through gate 610, allowing fluid in second fluid chamber 618b to be expelled through gate 610 and through outlet 608, as illustrated by flow indicating arrows 702. Fluid in second fluid chamber 618b can be expelled by, for example and without limitation, centripetal force, gas pressure, physical pressure, including manual activation, gravitational force, or combinations thereof, optionally including a second plunger.

Based on the description herein, one skilled in the relevant art(s) will understand that gate 610 can be implemented with other configurations as well, including configurations where gate 610, or a portion thereof, is implemented within plunger 612. Such other configurations are within the spirit and scope of the present disclosure.

One or more additional plungers and corresponding gates are optionally implemented. Additional fluid chambers can be controlled to serially dispense fluids therein, sequentially or out-of-order, and/or to internally mix fluids from multiple fluid chambers. Example embodiments are described below for illustrative purposes.

Pump 600 may be operated in reverse as a vacuum device.

2. Serial Dispensing

Figure 9:
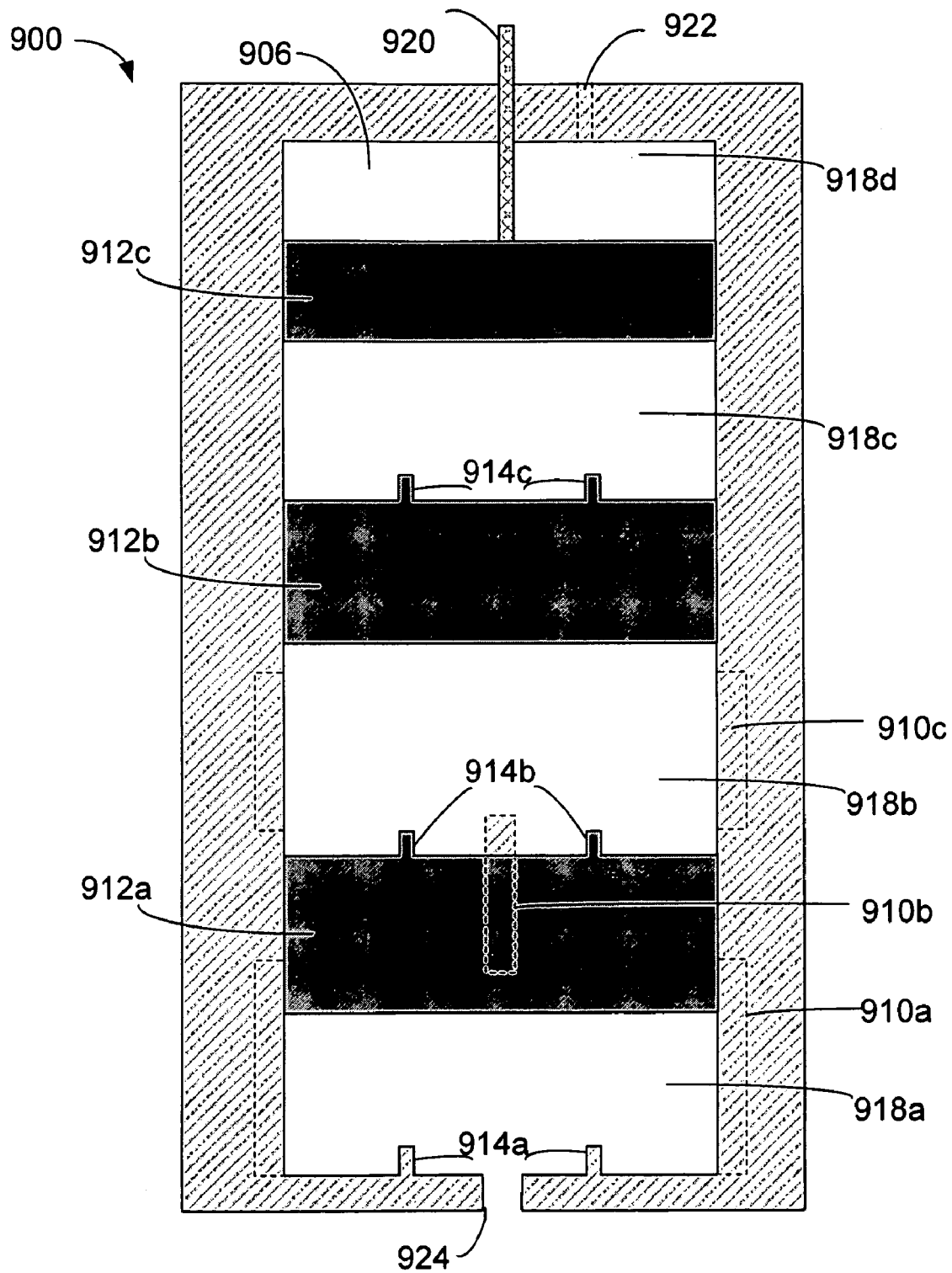
FIG. 9 is a cross-sectional block diagram of a multi-chamber pump 900.
Figure 10:
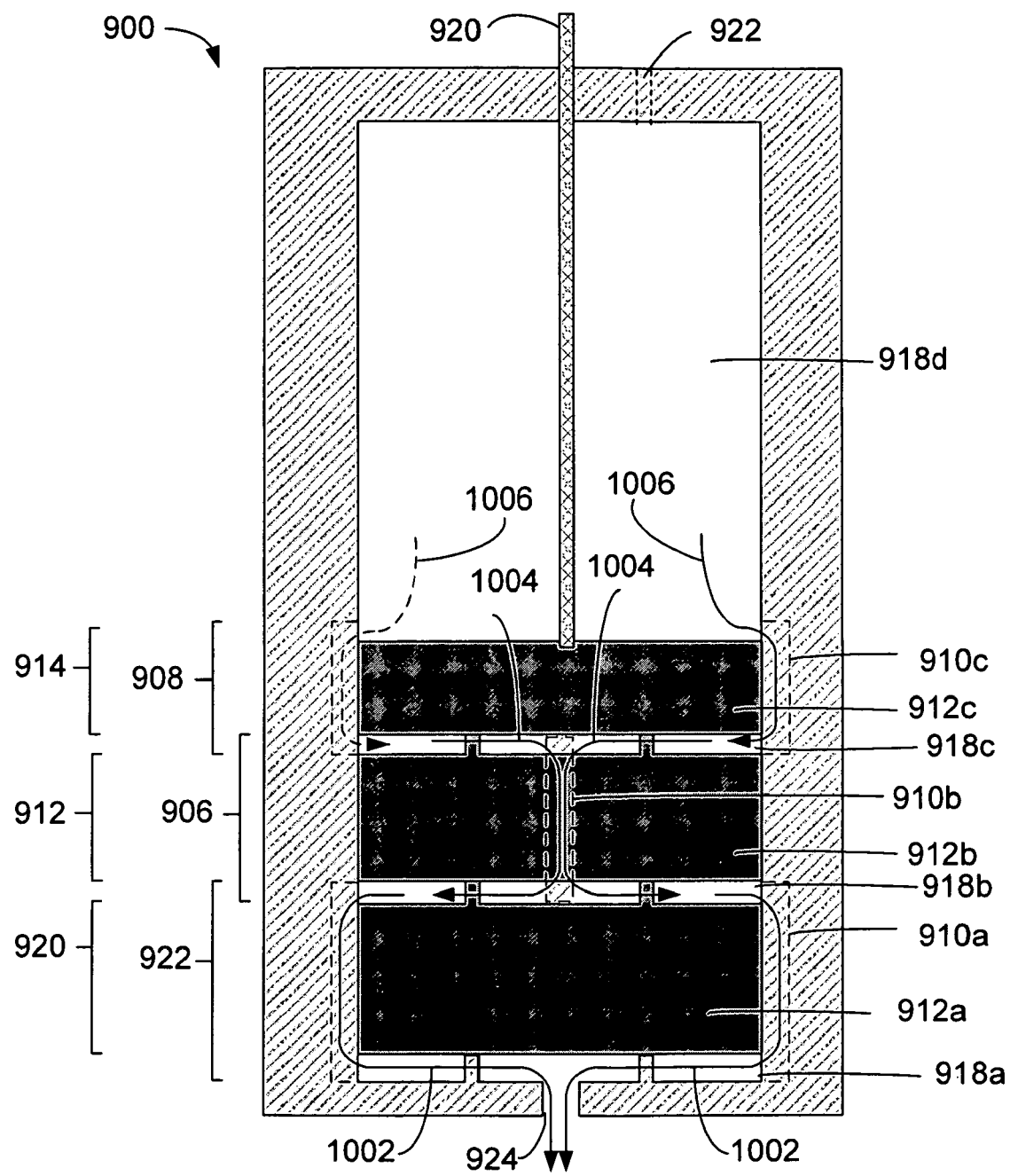
FIG. 10 is another cross-sectional block diagram of pump 900.

FIGS. 9 and 10 are cross-sectional block diagrams of an exemplary multiple fluid chamber, serially dispensing pump 900. Pump 900 includes plungers 912a, 912b, and 912c, defining fluid chambers 918a through 918d. Pump 900 further includes stops 914a through 914c, which can be configured similar to, or different than stop 614 in FIGS. 6, 7 and 8.

In the example of FIGS. 9 and 10, plungers 912a through 912c are longitudinally aligned with one another within a housing cavity 906, and are movable between functionally closed positions, as illustrated in FIG. 9, and functionally open positions, as illustrated in FIG. 10. The functionally open and closed positions of plungers 912a, 912b, and 912c are generally defined with respect to whether they allow or retard fluid communication with respect to one or more fluid chambers.

Pump 900 includes gates 910a through 910c. In FIG. 9, when plunger 912a is in its functionally open position, fluid chambers 918a and 918b are in fluid communication with one another through gate 910a. In FIG. 10, when plunger 912b is in its functionally open position, fluid chambers 918b and 918c are in fluid communication with one another through gate 910b. When plunger 912c is in its functionally open position, fluid chambers 918c and 918d are in fluid communication with one another through gate 910c.

Plungers 912a through 912c and gates 910a through 910c are configured, dimensioned, positioned, and/or controlled to allow fluids within the fluid chambers 918a through 918d to be expelled or dispensed serially. Exemplary methods and systems for controlling plungers 912 are described below.

In the example of FIGS. 9 and 10, gates 910a through 910c have respective gate lengths 922, 906, and 908 (FIG. 10). Gate length 922 is greater than gate length 906, which is greater than gate length 908. Gates 910a through 910c are laterally dispersed from one another so as not to interfere with one another. A portion of gate 910a longitudinally overlaps a portion of gate 910b. A portion of gate 910b longitudinally overlaps a portion of gate 910c. Plungers 912a through 912c have respective edge heights 920, 912, and 914. Edge height 920 is greater than edge height 912, which is greater than edge height 914. Gate length 122 is greater than edge height 920. Gate length 906 is greater than edge height 912. Gate length 908 is greater than edge height 914. Other dimensions may be implemented.

In operation, as plunger 112a moves from its functionally closed position to its functionally open position, fluid in fluid chamber 918a is expelled through outlet 924. Outlet 924 may lead to one or more other fluid chambers, which may include one or more of a sample substrate and an assay substrate. Plungers 912b and 912c typically move together with plunger 912a, thereby maintaining a substantially constant volume in each of fluid chambers 918b through 918c.

When plunger 912a reaches its functionally open position, fluid chamber 918b is in fluid communication with fluid chamber 918a and outlet 908 through gate 910a. Plunger 912b is then moved from its functionally closed position to its functionally open position, thereby expelling or dispensing fluid in fluid chamber 918b through gate 910a and outlet 908, as illustrated at 1002 in FIG. 10.

When plunger 912b reaches its functionally open position, fluid chamber 918c is in fluid communication with fluid chamber 918b through gate 910b, and is thus in fluid communication with fluid chamber 918a and outlet 908 through gate 910a. Plunger 912c is then moved from its functionally closed position to its functionally open position, thereby expelling or dispensing fluid in fluid chamber 918c through gate 910b, gate 910a, and outlet 908, as illustrated at 1004 and 1002 in FIG. 10.

When plunger 912c reaches its functionally open position, fluid chamber 918d is in fluid communication with fluid chamber 918c through gate 910c, and is thus in fluid communication with fluid chamber 918b through gate 910b, and fluid chamber 918a and outlet 908 through gate 910a. Fluid in fluid chamber 918d is then expelled or dispensed through gates 910c, 910b, and 910a, and outlet 908, as illustrated at 1006, 1004, and 1002 in FIG. 10.

Movement of plungers 912 can be controlled in one or more of a variety of ways. For example, pump 900 can include a stem 920 (FIG. 9) coupled to plunger 912c to control plunger 912c through applied force, such as a compressed spring or other mechanical actuator, and/or an inlet 922 to apply a gas and/or fluid pressure and/or vacuum to fluid chamber 918d.

As stem 920 is moved into cavity 906, and/or as gas or fluid pressure is applied through inlet 922, plunger 912 is forced in the direction of outlet 908. Since the plungers 912 are in functionally closed positions, resultant pressure in fluid chamber 918c forces plunger 912b in the direction of outlet 908, which increases pressure in fluid chamber 918b, which forces plunger 912a in the direction of outlet 908, dispensing fluid from fluid chamber 918a through outlet 908. Continued force/pressure applied by stem 920 and/or inlet 922 cause plungers 912b and 912c to continue to move as described above, serially dispensing fluid from fluid chamber 918b, then from fluid chamber and 918c.

Based on the description herein, one skilled in the relevant art(s) will understand that a multiple fluid, serial output, dispenser or pump can be implemented with other housing shapes and forms, and other plunger alignment, movement, and control schemes.

3. Serial Mixing

FIGS. 11 through 14 are cross-sectional block diagrams of an exemplary multiple fluid chamber, serial mixing pump 1100.

Pump 1100 includes plungers 1112a through 1112d, fluid chambers 1118a through 1118c, and gates 1110a through 1110c. In the example below, plungers 1112a through 1112d are controlled to move fluid from fluid chamber 1118c to fluid chamber 1118a, then to move fluid from fluid chamber 1118b to fluid chamber 1118a, where the fluids mix. The mixed fluid in fluid chamber 1118a is then pumped to another fluid chamber through gate 1110a, or/or expelled through an outlet, The outlet may lead to one or more other fluid chambers, which may include one or more of a sample substrate and an assay substrate.

Figure 11:
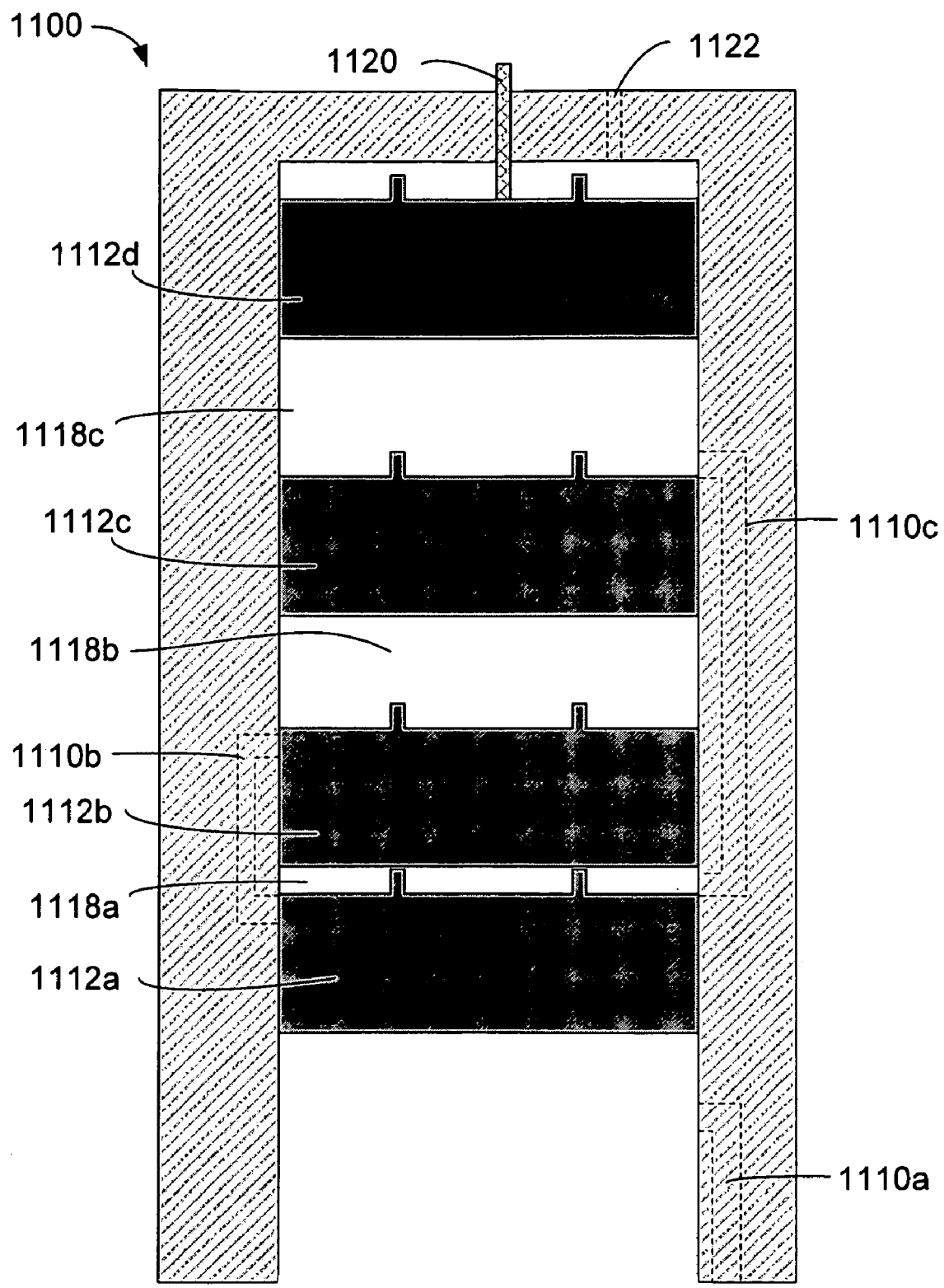
FIG. 11 is a cross-sectional block diagram of a pump 1100 configured to serially mix fluids from multiple fluid chambers.

FIG. 11 illustrates pump 1100 at an initial state.

Figure 12:
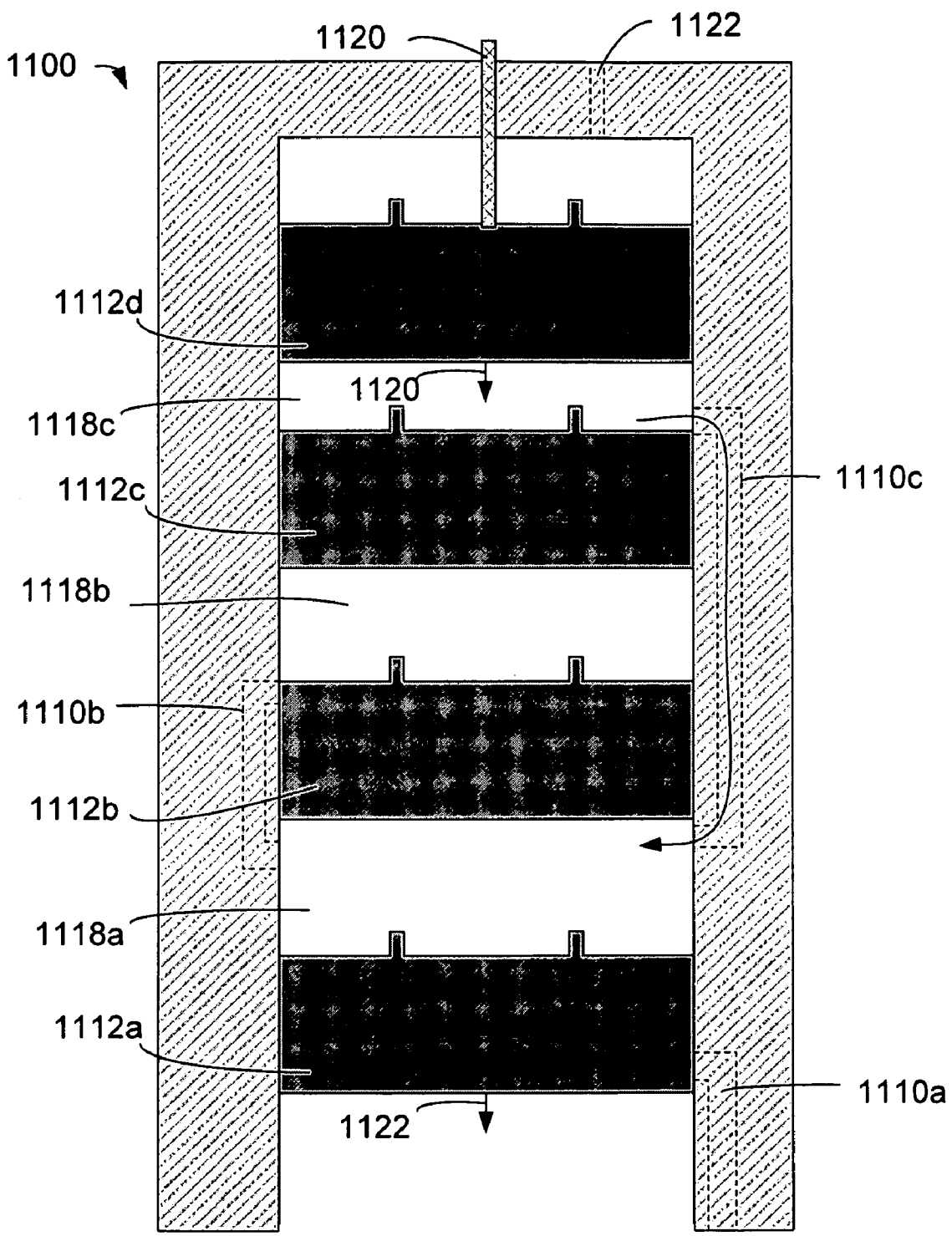
FIG. 12 is another cross-sectional block diagram of pump 1100.

FIG. 12 illustrates pump 1100 as plunger 1112d moves in the direction of arrow 1120, moving fluid from fluid chamber 1118c to fluid chamber 1118a through gate 1110c. Plunger 1112a simultaneously moves in the direction of arrow 1122 to accommodate fluid from fluid chamber 1118c.

Figure 13:
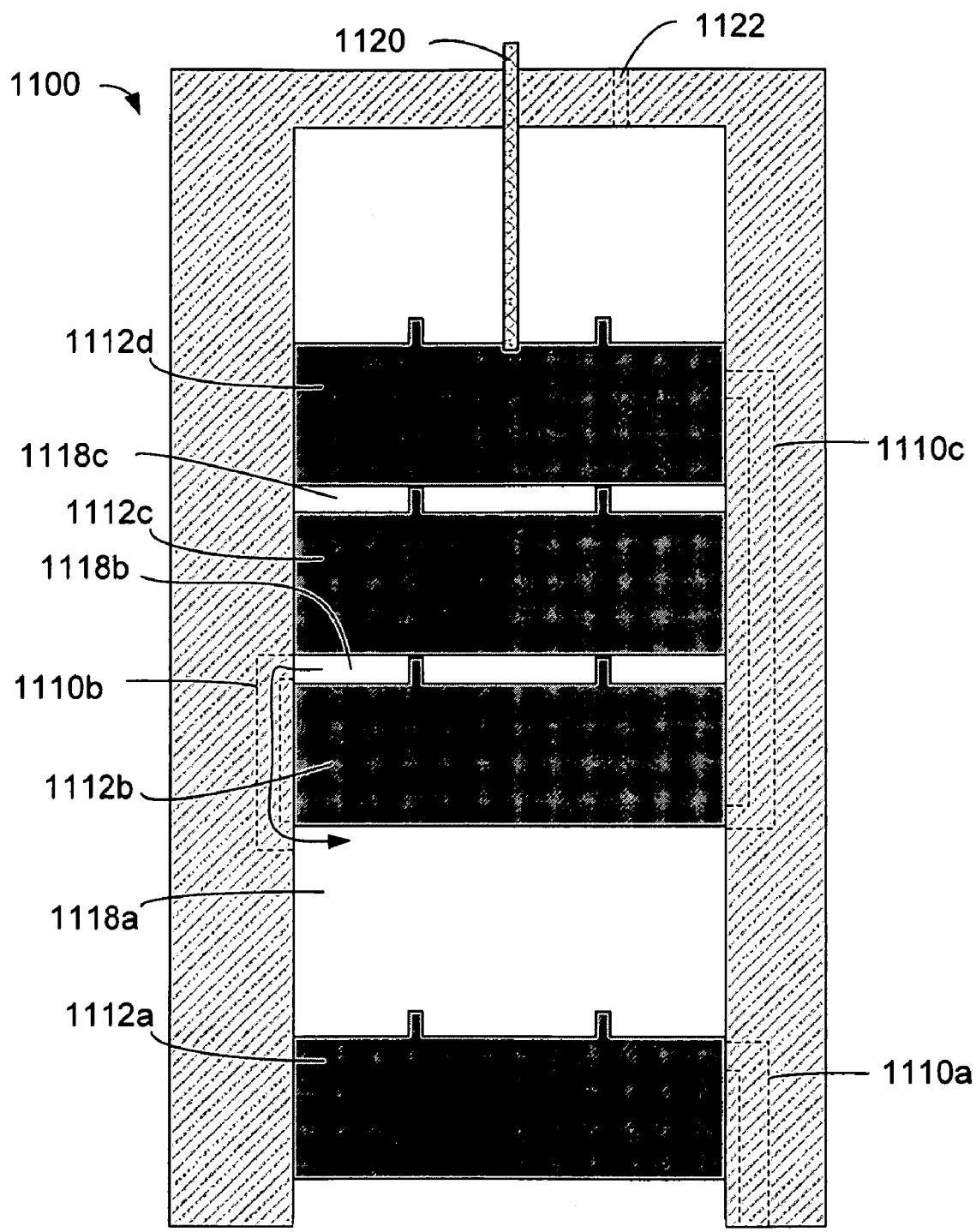
FIG. 13 is another cross-sectional block diagram of pump 1100.

When plunger 1112d reaches plunger 1112c, plungers 1112c and 1112b move in tandem with plunger 11122, whereby gate 1110c is sealed by plunger 1112d and gate 1110b is opened by plunger 1112b. Plungers 1112c and 1112d continue moving, thereby expelling fluid in fluid chamber 1118b to fluid chamber 1118a, where it mixes with the fluid from fluid chamber 1118c, as illustrated in FIG. 13. Plunger 1112a continues to move as well, thereby accommodating the fluid from fluid chamber 1118b.

Figure 14:
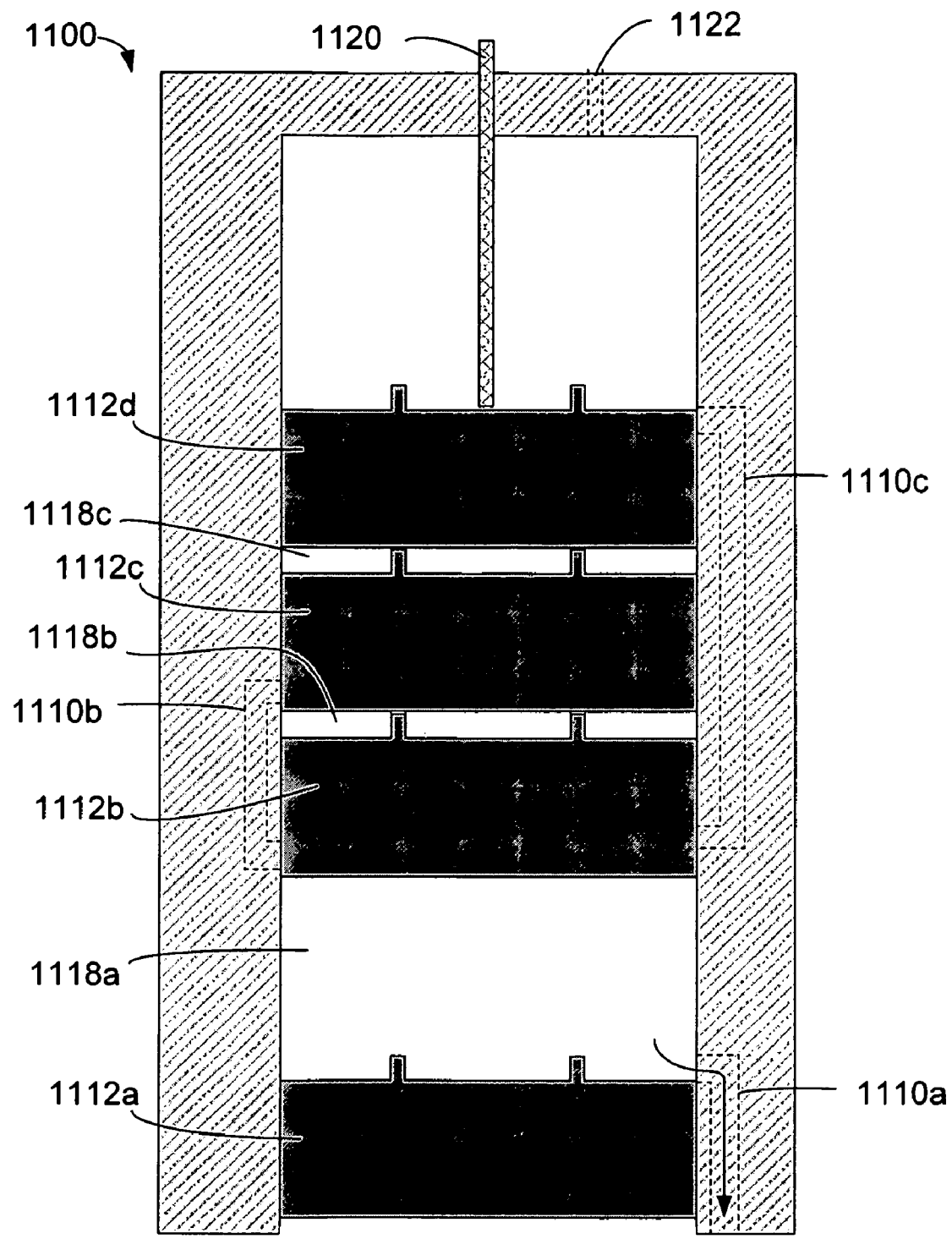
FIG. 14 is another cross-sectional block diagram of pump 1100.

In FIG. 14, plunger 1112a moves slightly more, thereby opening gate 1110a. Plunger 1112b, and optionally plungers 1112c and 1112d move to expel the fluid in fluid chamber 1118a through gate 1110a. Gate 1110a may lead to one or more other fluid chambers, which may include one or more of a sample substrate and an assay substrate.

Movement of plungers 1112 can be controlled in one or more of a variety of ways. For example, pump 1100 can include a stem 1120 coupled to plunger 1112d, and/or an inlet 1122, to control plungers 1112 substantially as described above with respect to pump 900. Control of plungers 1112 is not, however, limited to the examples of stem 1120 or inlet 1122.

4. Simultaneous Mixing

Figure 15:
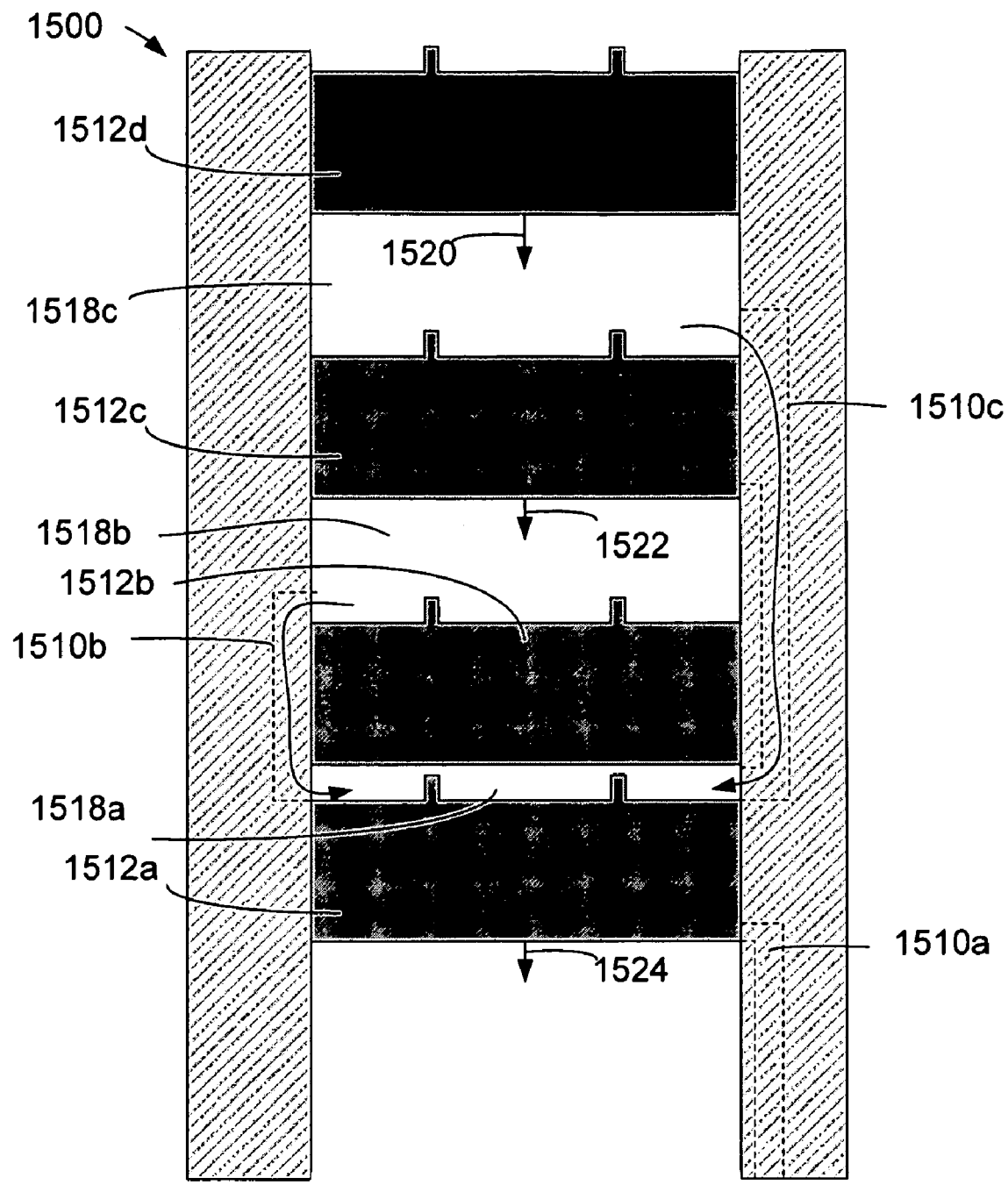
FIG. 15 is a cross-sectional block diagram of a pump 1500 configured to simultaneously mix fluids from multiple fluid chambers.
Figure 16:
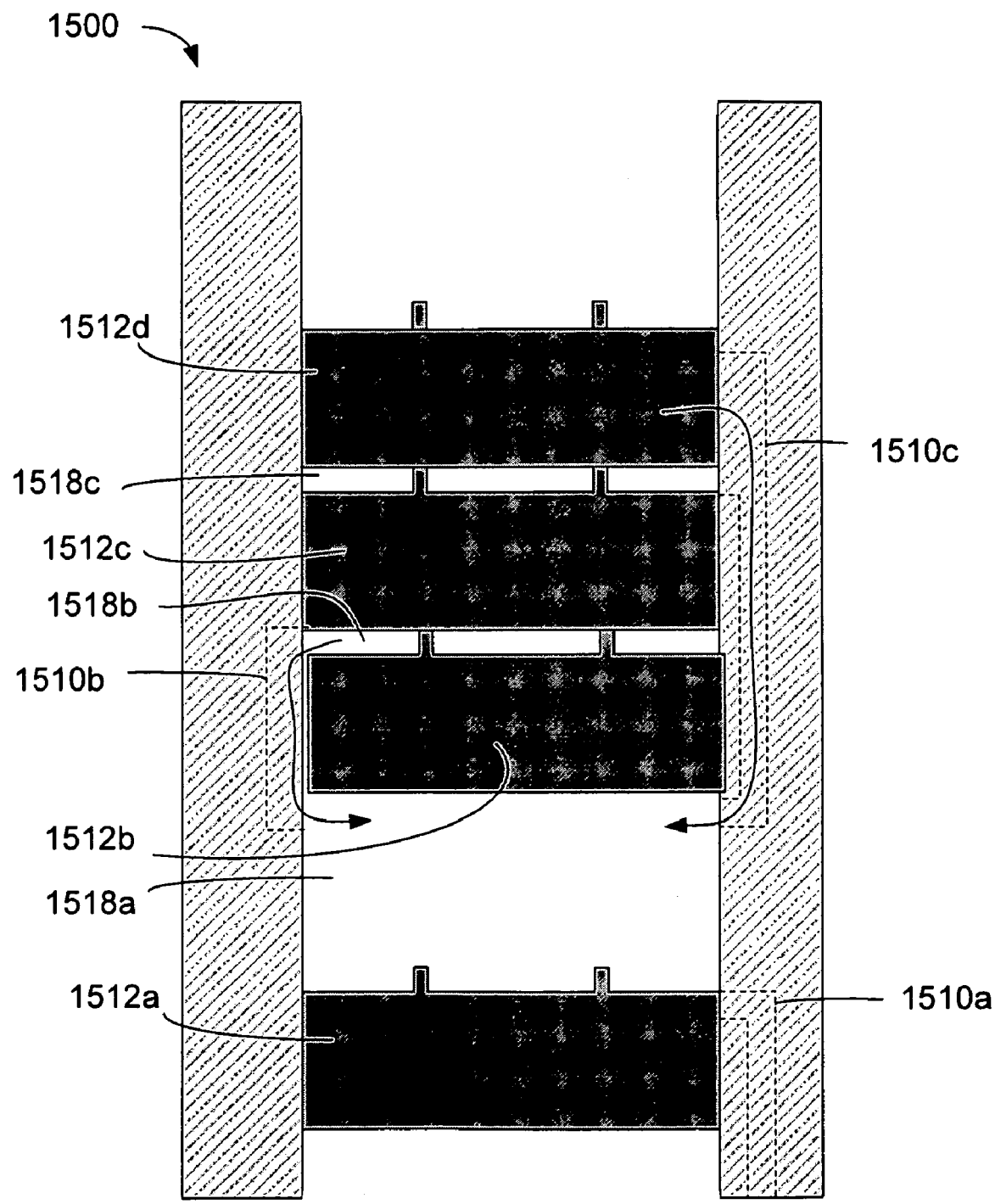
FIG. 16 is another cross-sectional block diagram of pump 1500.
Figure 17:
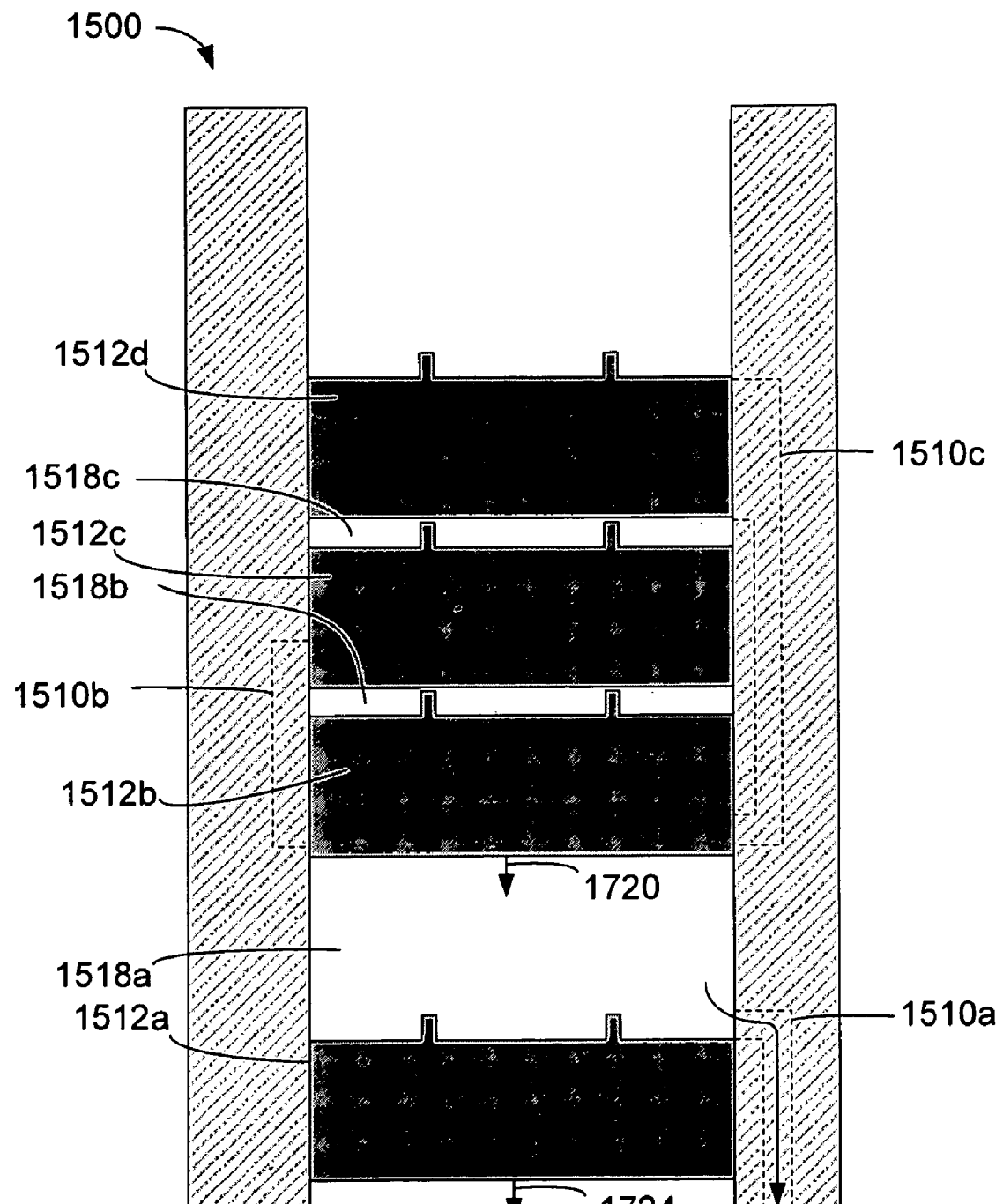
FIG. 17 is another cross-sectional block diagram of pump 1500.

FIGS. 15 through 17 are cross-sectional block diagrams of an exemplary multiple fluid chamber, simultaneous mixing pump 1500.

Pump 1500 includes plungers 1512a through 1512d, fluid chambers 1518a through 1518c, and gates 1510a through 1510c. In the example below, plungers 1512a through 1512d are controlled to simultaneously move fluid from fluid chambers 1518b and 1518c to fluid chamber 1518a, where they mix with one another. The mixed fluid in fluid chamber 1518a is then pumped to another fluid chamber through gate 1510a, or/or expelled through an outlet. The outlet may lead to one or more other fluid chambers, which may include one or more of a sample substrate and an assay substrate.

In FIGS. 15 and 16, plunger 1512d moves in the direction of arrow 1520, moving fluid from fluid chamber 1518c to fluid chamber 1518a through gate 1510c. Simultaneously, plunger 1512c moves in the direction of arrow 1722, moving fluid from fluid chamber 1518b to fluid chamber 1518a through gate 1510b. Plunger 1512a simultaneously moves in the direction of arrow 1524 so that fluid chamber 1518a accommodates the fluids from fluid chambers 1518b and 1818c.

In FIGS. 15 and 16, plunger 1512a seals gate 1510a. In FIG. 17, after the fluids from fluid chambers 1518b and 1518c have moved into fluid chamber 1518a, plunger 1512a moves in the direction of arrow 1524, thereby opening gate 1510a, and plunger 1512b moves in the direction of arrow 1720, thereby closing gates 1510b and 1510c. Plunger 1512b, and optionally plungers 1512c and 1512d, continues to move in the direction of arrow 1720, thereby expelling the mixed fluid in fluid chamber 1518a, through gate 1510a.

Movement of plungers 1512 can be controlled in one or more of a variety of ways, such as described above with respect to pump 400, and/or as described below with respect to FIGS. 16-19. Control of plungers 1512 is not, however, limited to these examples.

5. Simultaneous Mixing, Opposing Directions

Figure 18:
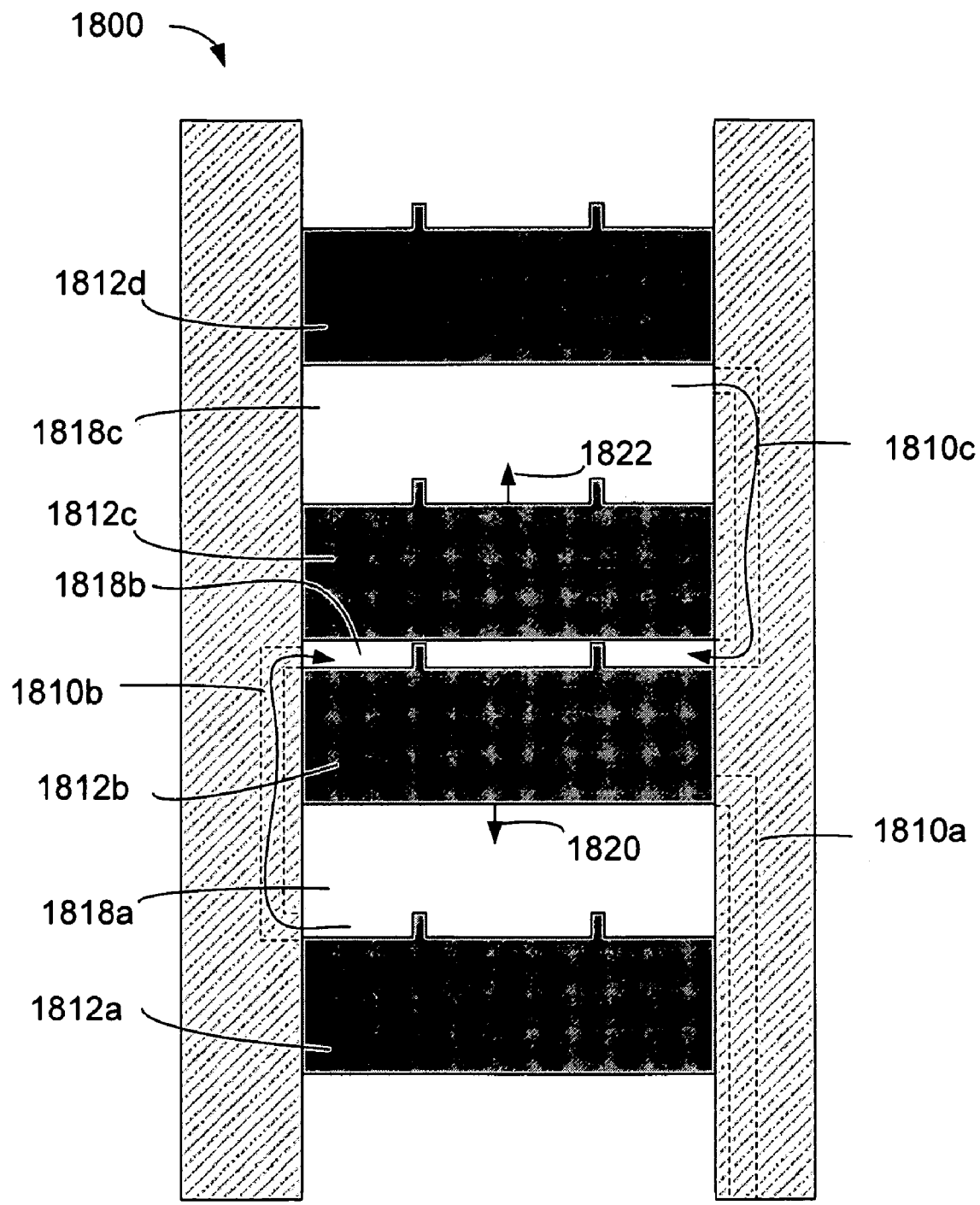
FIG. 18 is a cross-sectional block diagram of a pump 1800 configured to simultaneously mix fluids from multiple fluid chambers.
Figure 19:
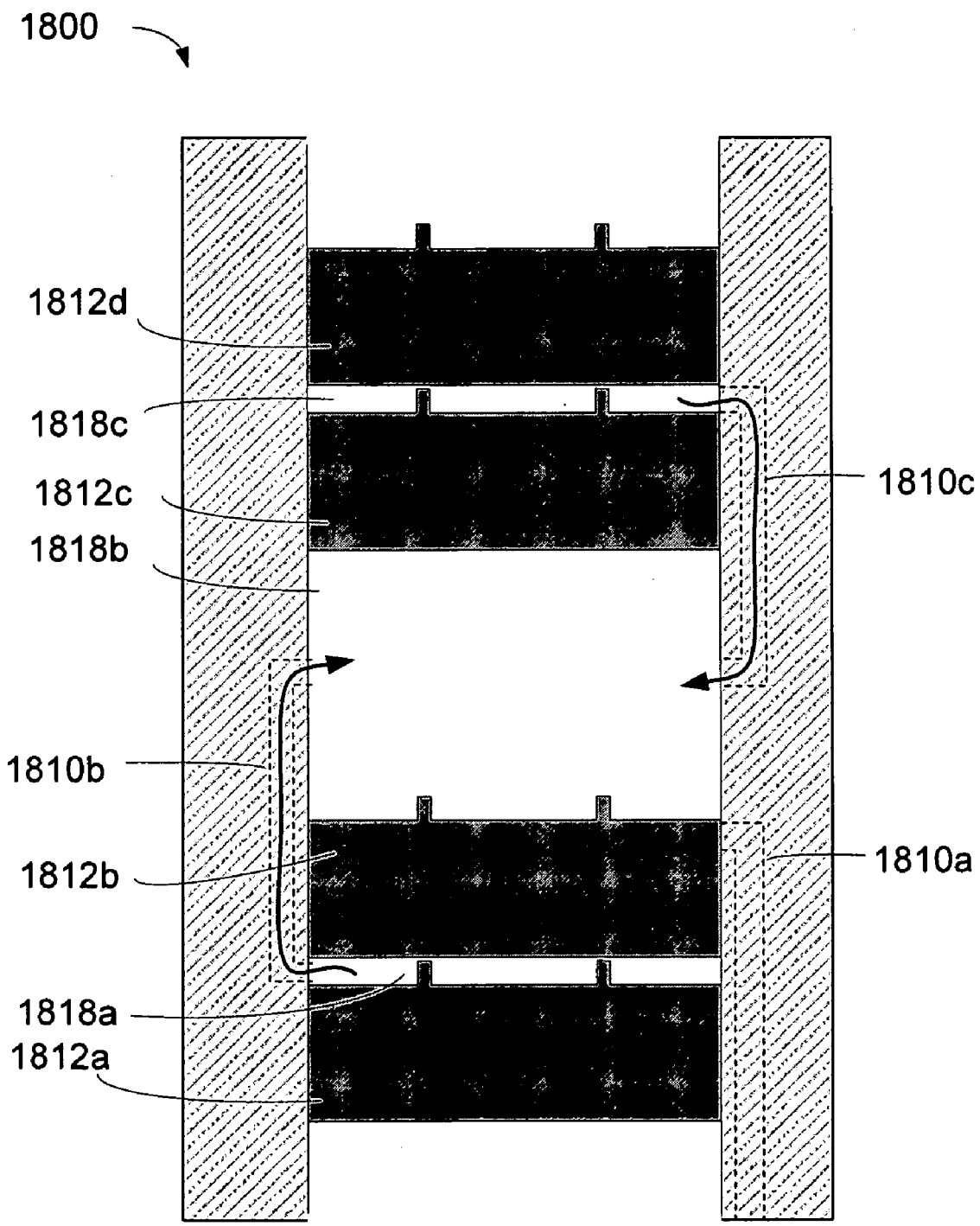
FIG. 19 is another cross-sectional block diagram of pump 1800.
Figure 20:
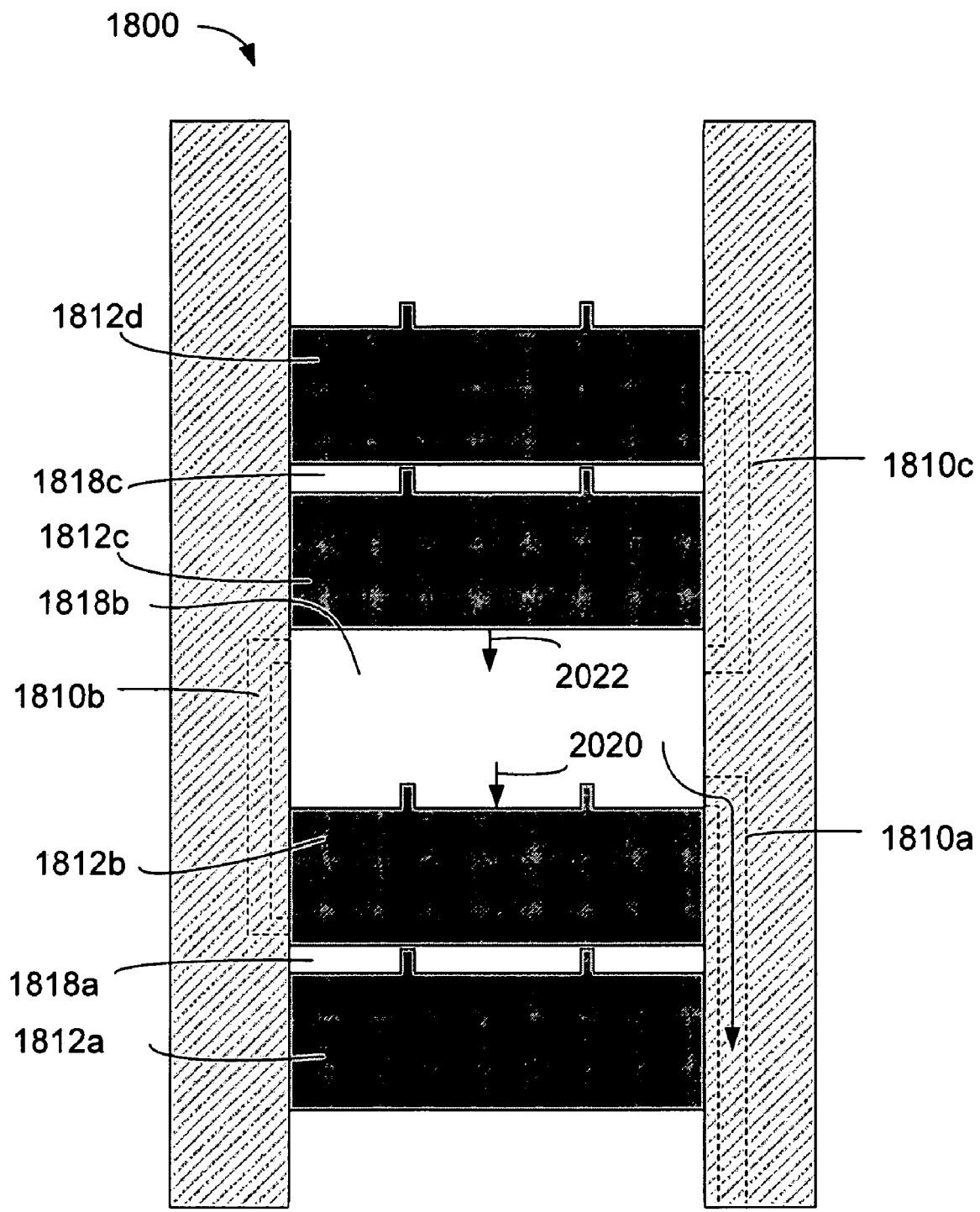
FIG. 20 is another cross-sectional block diagram of pump 1800.

FIGS. 18 through 20 are cross-sectional block diagrams of an exemplary multiple fluid chamber, simultaneous mixing pump 1800, in which fluids flow from opposing directions into a mixing chamber.

Pump 1800 includes plungers 1812a through 1812d, fluid chambers 1818a through 1818c, and gates 1810a through 1810c. In the example below, plungers 1812b and 1812c are controlled to simultaneously move fluid from fluid chambers 1818a and 1818c to fluid chamber 1818b, where they mix with one another. The mixed fluid in fluid chamber 1818b is then pumped to another fluid chamber through gate 1810a, or/or expelled through an outlet.

In FIGS. 18 and 19, plunger 1812b moves in the direction of arrow 1820, moving fluid from fluid chamber 1818a to fluid chamber 1818b through gate 1810b. Simultaneously, plunger 1812c moves in the direction of arrow 1822, moving fluid from fluid chamber 1818c to fluid chamber 1818b through gate 1810c.

In FIGS. 18 and 19, plunger 1812b seals gate 1810a. In FIG. 20, after the fluids from fluid chambers 1818a and 1818c have moved into fluid chamber 1818b, plungers 1812a and 1812b move slightly in the direction of arrow 2020, thereby opening gate 1810a. Plunger 1812c, and optionally plunger 1812d move in the direction of arrow 2022, thereby expelling the mixed fluid in fluid chamber 1818b through gate 1810a.

Movement of plungers 1812 can be controlled in one or more of a variety of ways, such as described above with respect to pump 400. Control of plungers 1812 is not, however, limited to these examples.

6. Nested Plungers

Figure 22:
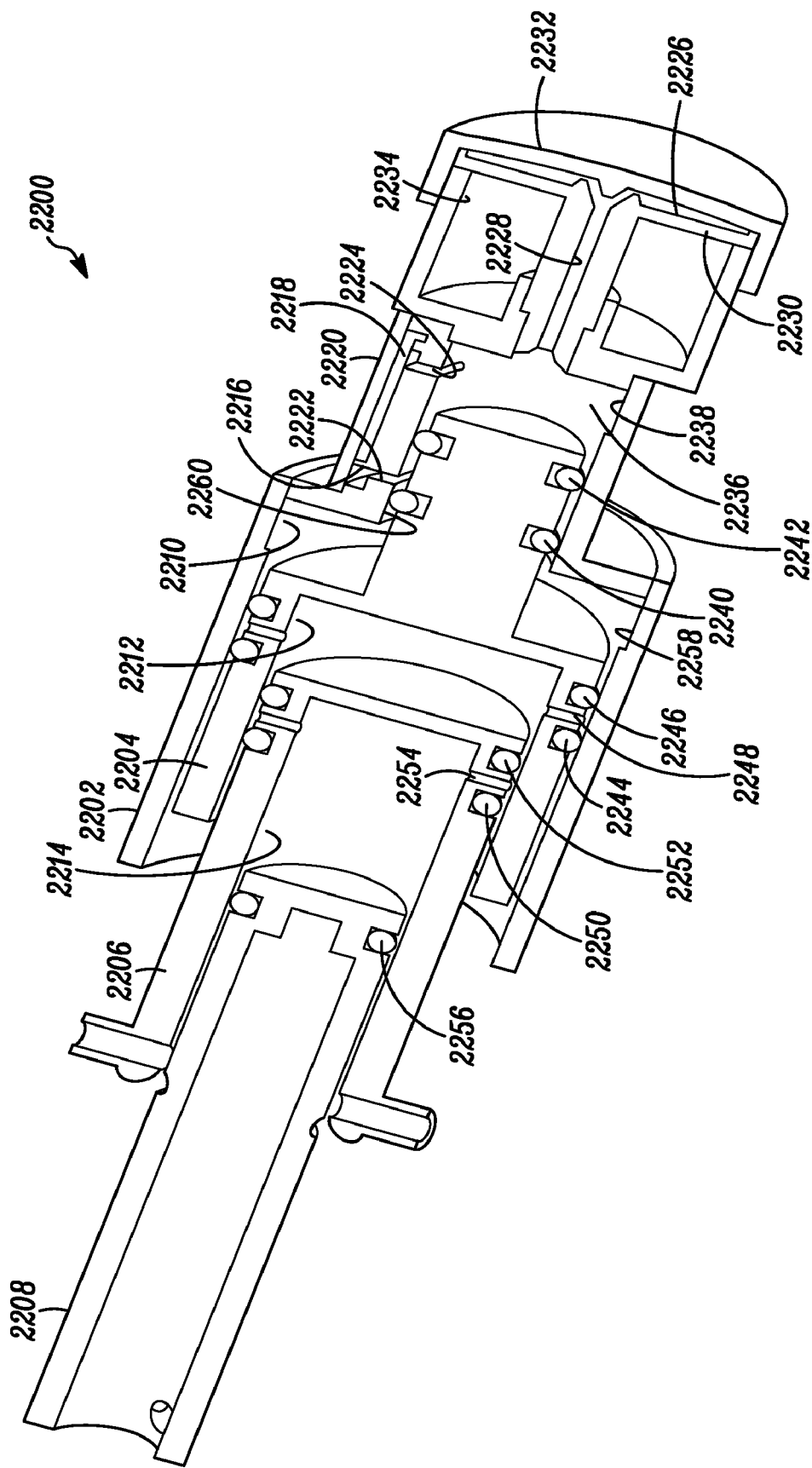
FIG. 22 is a cross-sectional perspective view of an exemplary assay system 2200.

FIG. 22 is a cross-sectional perspective view of a portion of an exemplary assay system 2200 including a housing portion 2202 and a fluid controller system, including a plurality of fluid controllers, or plungers 2204, 2206, and 2208. Fluid controllers 2204, 2206, and 2208 define a plurality of fluid chambers, illustrated here as first, second, and third fluid chambers 2210, 2212, and 2214, respectively. Fluid controllers 2204, 2206, and 2208 are slideably nested within one another.

Housing portion 2202 includes a sample chamber 2216 to receive a sample, and may include a sample substrate, membrane or pad 2218. Housing portion 2202 may include a cover mechanism such as a cover portion 2220, which may be removable or hingedly coupled to housing portion 2202, as described above with respect to FIG. 3. Housing portion 2202 includes a sample chamber inlet 2222 and a sample chamber outlet 2224.

Housing portion 2202 includes an assay chamber 2226 and an assay chamber inlet 2228, and may include an assay substrate, membrane or pad 2228 to capture, react, and/or display assay results.

Housing portion 2202 includes an assay result viewer, illustrated here as a display window 2232 disposed over assay chamber 2228.

Housing portion 2202 includes a waste fluid chamber 2234 to receive fluids from assay chamber 2226.

Housing portion 2202 includes a transient fluid chamber 2236 having one or more fluid channels 2238, also referred to herein as a fluid controller bypass channel.

Housing portion 2202 further includes one or more other fluid channels 2258.

First fluid chamber 2210 includes a fluid chamber outlet 2260, illustrated here as a space between fluid controller 2206 and an inner surface of hosing portion 2202.

Second fluid chamber 2212 includes a fluid chamber outlet 2248, illustrated here as a gate or passage through fluid controller 2204.

Third fluid chamber 2214 includes a fluid chamber outlet 2254, illustrated here as a gate through fluid controller 2206.

Fluid controllers 2204, 2206, and 2208 include one or more sealing mechanisms, illustrated here as O-rings 2240 and 2242, O-rings 2244 and 2246, O-rings 2250 and 2252, and O-ring 2256.

Exemplary operation of assay system 2200 is described below with respect to FIGS. 23-27.

Figure 23:
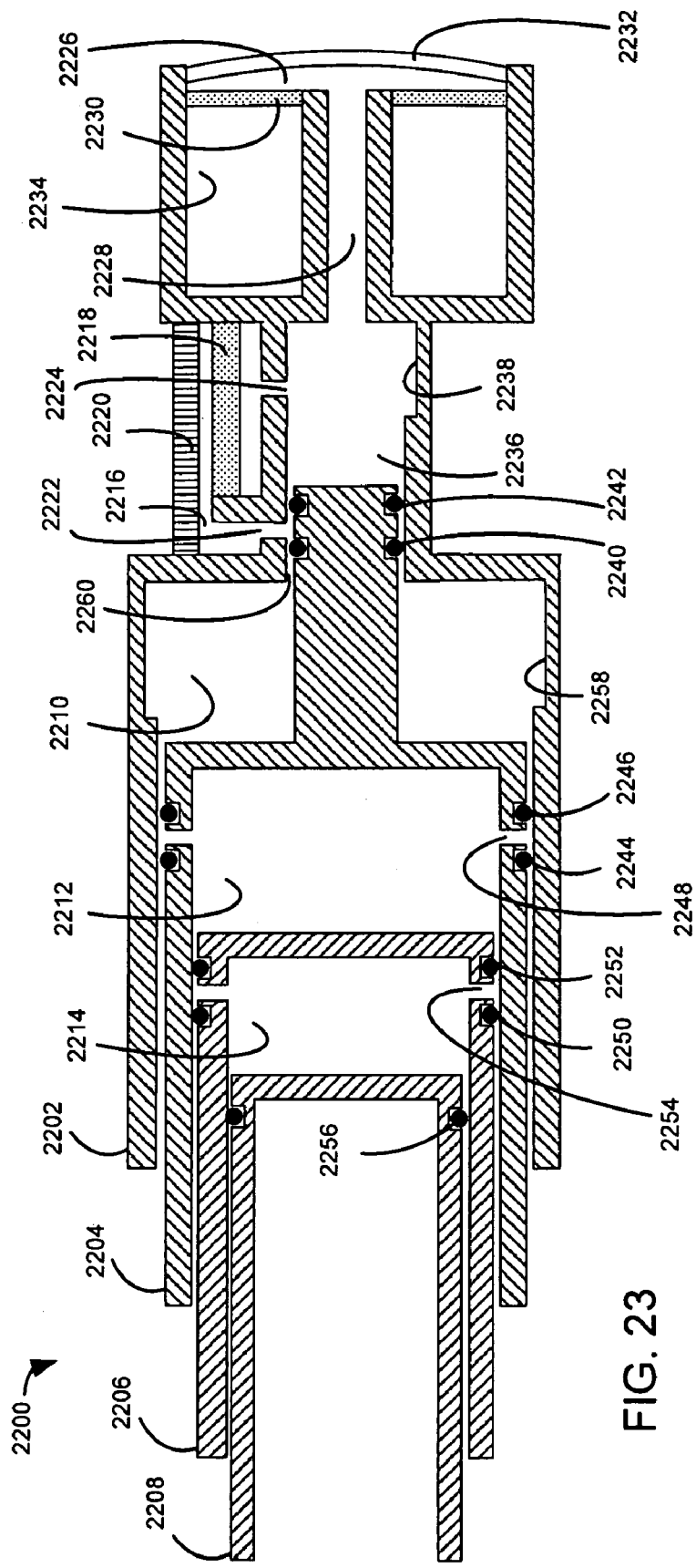
FIG. 23 is a cross-sectional block diagram of assay system 2200.

FIG. 23 is a cross-sectional block diagram of assay system 2200, wherein fluid controllers 2204, 2206, and 2208 are illustrated in corresponding initial or functionally closed first positions. When fluid controllers 2204, 2206, and 2208 are in the initial positions, O-ring 2240 is sealingly engaged against an inner surface of housing portion 2202, between first fluid chamber outlet 2260 and sample chamber inlet 2222, to substantially preclude fluid flow from fluid chamber 2210. Similarly, O-rings 2244 and 2246 are sealingly engaged against an inner surface of housing portion 2202 to substantially preclude fluid flow from fluid chamber 2212 through second fluid chamber outlet 2248. O-rings 2250 and 2252 are sealingly engaged against an inner surface of housing portion 2202 to substantially preclude fluid flow from fluid chamber 2214 through third fluid chamber outlet 2254.

O-Rings 2244, 2246, 2250, 2252, and 2256 cause fluid controllers 2204, 2206, and 2208 to be pressurizably engaged with one another, such that a force applied to fluid controller 2208, in the direction of fluid controllers 2206 and 2204, causes the fluid controller system to serially move into functionally open positions with respect to first, second, and third fluid chambers 2210, 2212, and 2214, as described below with respect to FIGS. 24-27.

Figure 24:
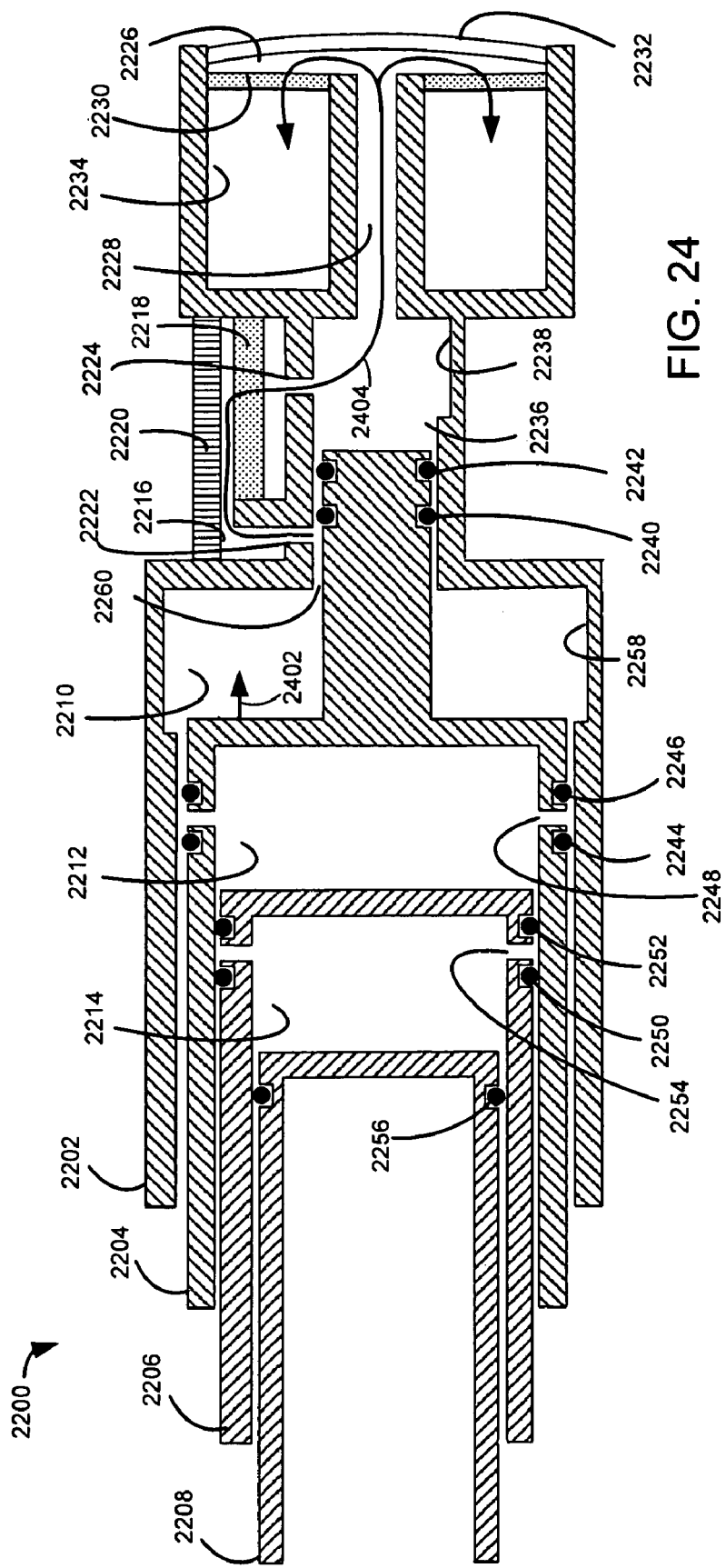
FIG. 24 is another cross-sectional block diagram of assay system 2200.

FIG. 24 is a cross-sectional block diagram of assay system 2200, wherein the fluid controller system has moved in a direction of arrow 2402, relative to housing portion 2202, to align first fluid chamber outlet 2260 with a fluid path 2404 to assay chamber 2226. This is referred to herein as a first functionally open position. Fluid path 2404 includes sample chamber inlet 2222, sample chamber 2216, sample chamber outlet 2224, transient fluid chamber 2236, and assay chamber inlet 2228.

As continued force is applied to fluid controller 2208, fluid controllers 2204, 2206, and 2208 continue to move in the direction of arrow 2402, to expel fluid from first fluid chamber 2210 to assay chamber 2226, through fluid path 2204. The fluid may flow over or through assay substrate 2230, to waste fluid chamber 2234.

Figure 25:
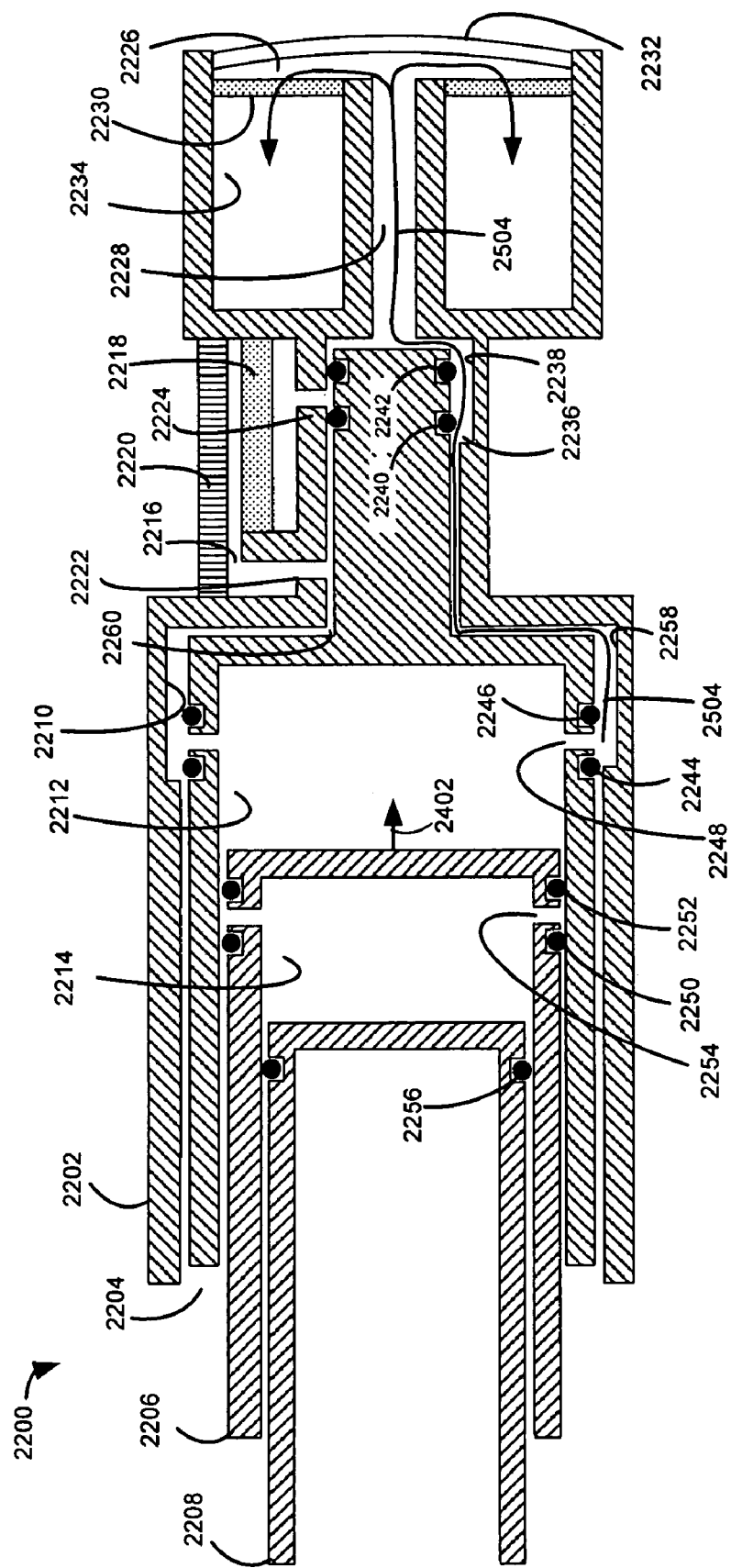
FIG. 25 is another cross-sectional block diagram of assay system 2200.

FIG. 25 is a cross-sectional block diagram of assay system 2200, wherein the fluid controller system has moved further in the direction of arrow 2402, to align second fluid chamber outlet 2248 with a fluid path 2504 to assay chamber 2226. This is referred to herein as a second functionally open position. Fluid path 2504 includes fluid channel 2258 to bypass O-ring 2246 and first fluid controller 2204, first fluid chamber outlet 2260, transient fluid chamber 2236, fluid channel 2238 to bypass O-rings 2240 and 2242, and assay chamber inlet 2228.

As continued force is applied to fluid controller 2208, fluid controllers 2206 and 2208 continue to move in the direction of arrow 2402, to expel fluid from second fluid chamber 2212 to assay chamber 2226, through fluid path 2504. The fluid may flow over or through assay substrate 2230, to waste fluid chamber 2234.

Figure 26:
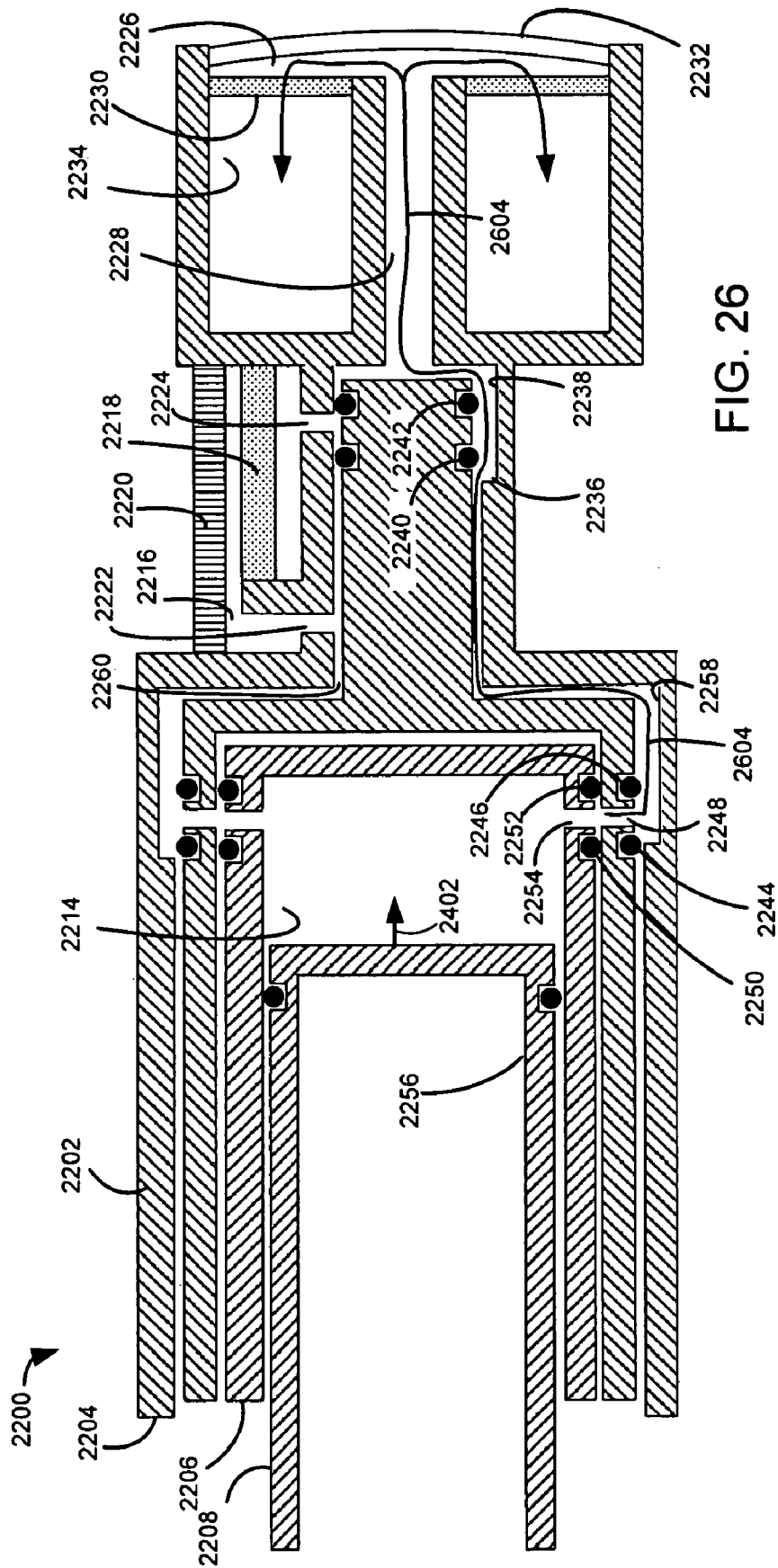
FIG. 26 is another cross-sectional block diagram of assay system 2200.

FIG. 26 is a cross-sectional block diagram of assay system 2200, wherein the fluid controller system has moved further in the direction of arrow 2402, to align third fluid chamber outlet 2254 with a fluid path 2604 to assay chamber 2226. This is referred to herein as a third functionally open position. Fluid path 2604 includes second fluid chamber outlet 2248, fluid channel 2258, first fluid chamber outlet 2260, transient fluid chamber 2236, and assay chamber inlet 2228.

As continued force is applied to fluid controller 2208, fluid controller 2208 continues to move in the direction of arrow 2402, to expel fluid from third fluid chamber 2214 to assay chamber 2226, through fluid path 2604. The fluid may flow over or through assay substrate 2230, to waste fluid chamber 2234.

Figure 27:
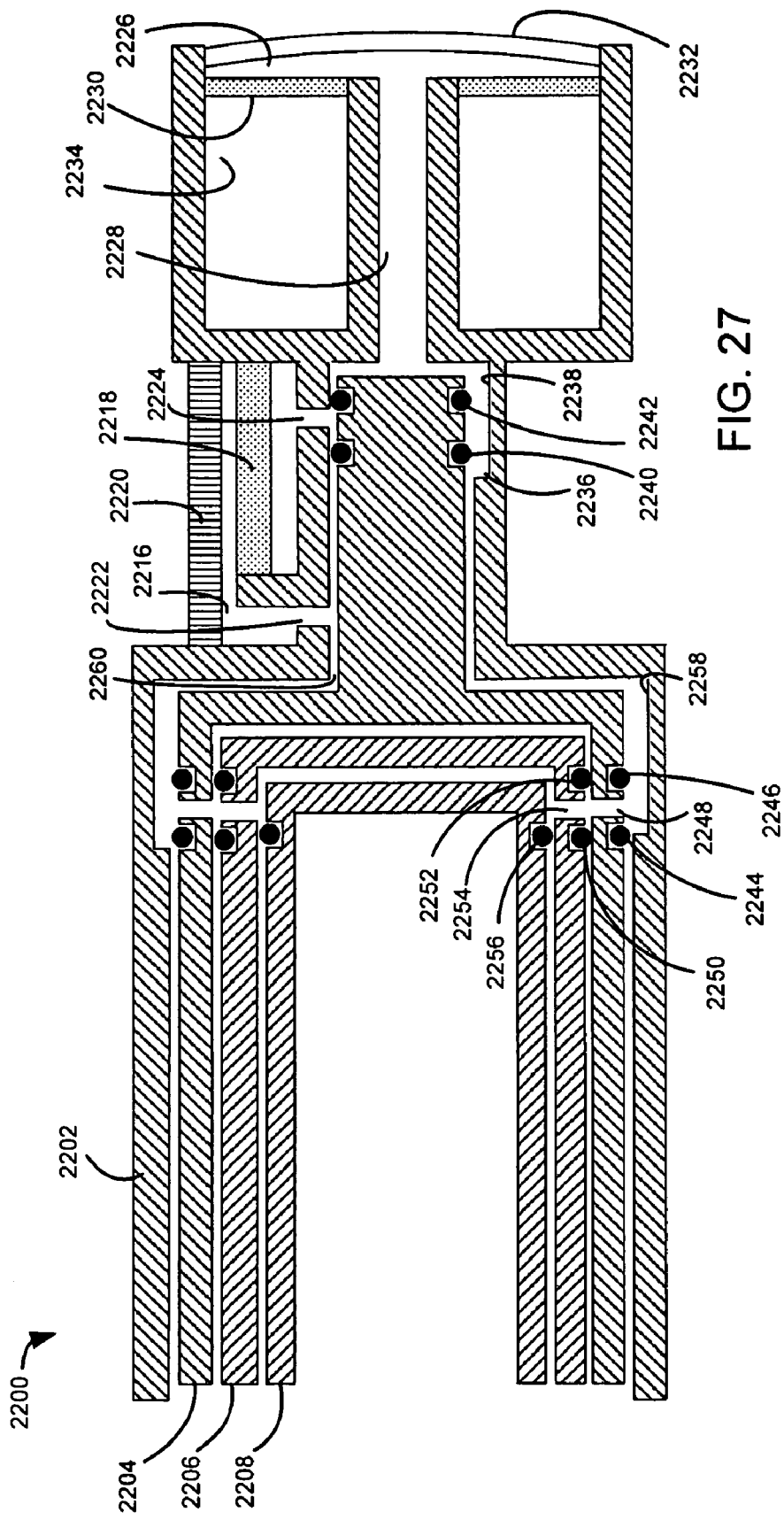
FIG. 27 is another cross-sectional block diagram of assay system 2200.

FIG. 27 is a cross-sectional block diagram of assay system 2200, wherein the fluid controller system has expelled fluid from third fluid chamber 2214.

Assay system 2200 may include an actuator system, which may be configured to act upon third fluid controller 2208.

Figure 28:
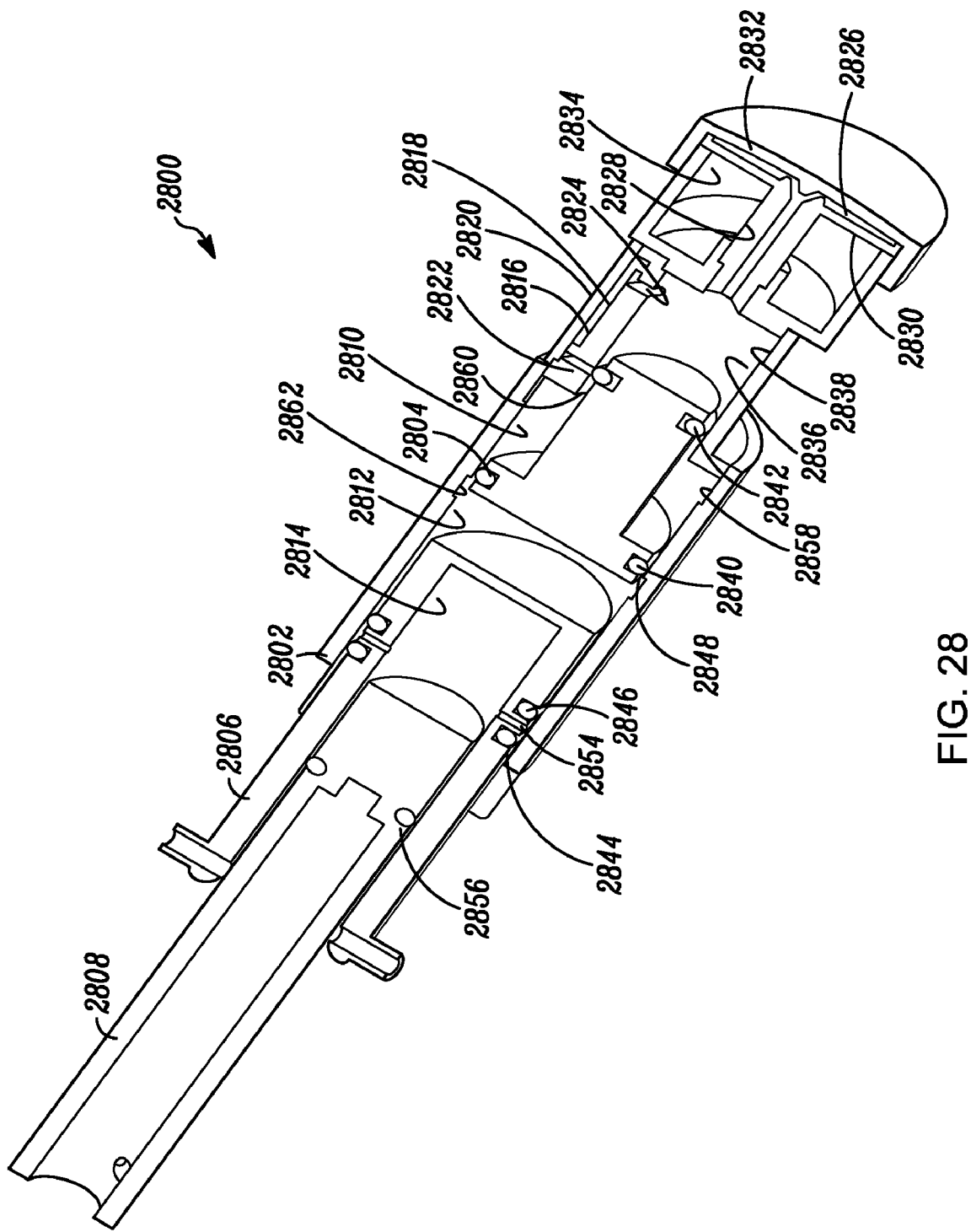
FIG. 28 is a cross-sectional perspective view of an exemplary assay system 2800.

FIG. 28 is a cross-sectional perspective view of a portion of an exemplary assay system 2800 including a housing portion 2802 and a fluid controller system, including a plurality of fluid controllers, or plungers 2804, 2806, and 2808. Fluid controllers 2804, 2806, and 2808 define a plurality of fluid chambers, illustrated here as first, second, and third fluid chambers 2810, 2812, and 2814, respectively. Fluid controller 2808 is slideably nested within fluid controller 2806.

Housing portion 2802 includes a sample chamber 2816 to receive a sample, and may include a sample substrate 2818, which may include a surface of sample chamber 2816 or membrane therein. Housing portion 2802 may include a cover mechanism such as a cover portion 2820, which may be removable or hingedly coupled to housing portion 2802, as described above with respect to FIG. 3. Housing portion 2802 includes a sample chamber inlet 2822 and a sample chamber outlet 2824.

Housing portion 2802 includes an assay chamber 2826 and an assay chamber inlet 2828, and may include an assay substrate 2828 to capture, react, and/or display assay results.

Assay substrate may include a surface of assay chamber 2826 or a membrane therein.

Housing portion 2802 includes an assay result viewer, illustrated here as a display window 2832 disposed over assay chamber 2828.

Housing portion 2802 includes a waste fluid chamber 2834 to receive fluids from assay chamber 2826.

Housing portion 2802 includes a transient fluid chamber 2836 having one or more fluid channels 2838, also referred to herein as a fluid controller bypass channel.

Housing portion 2802 further includes fluid channels 2858 and 2862.

First fluid chamber 2810 includes a fluid chamber outlet 2860, illustrated here as a space between fluid controller 2806 and an inner surface of hosing portion 2802.

Second fluid chamber 2812 includes a fluid chamber outlet 2848, illustrated here as a space between fluid controller 2804 and an inner surface of hosing portion 2802.

Third fluid chamber 2814 includes a fluid chamber outlet 2854, illustrated here as a gate or passage through fluid controller 2806.

Fluid controllers 2804, 2806, and 2808 include one or more sealing mechanisms, illustrated here as O-rings 2840 and 2842, O-rings 2844 and 2846, and O-ring 2856.

Exemplary operation of assay system 2800 is described below with respect to FIGS. 29-33.

Figure 29:
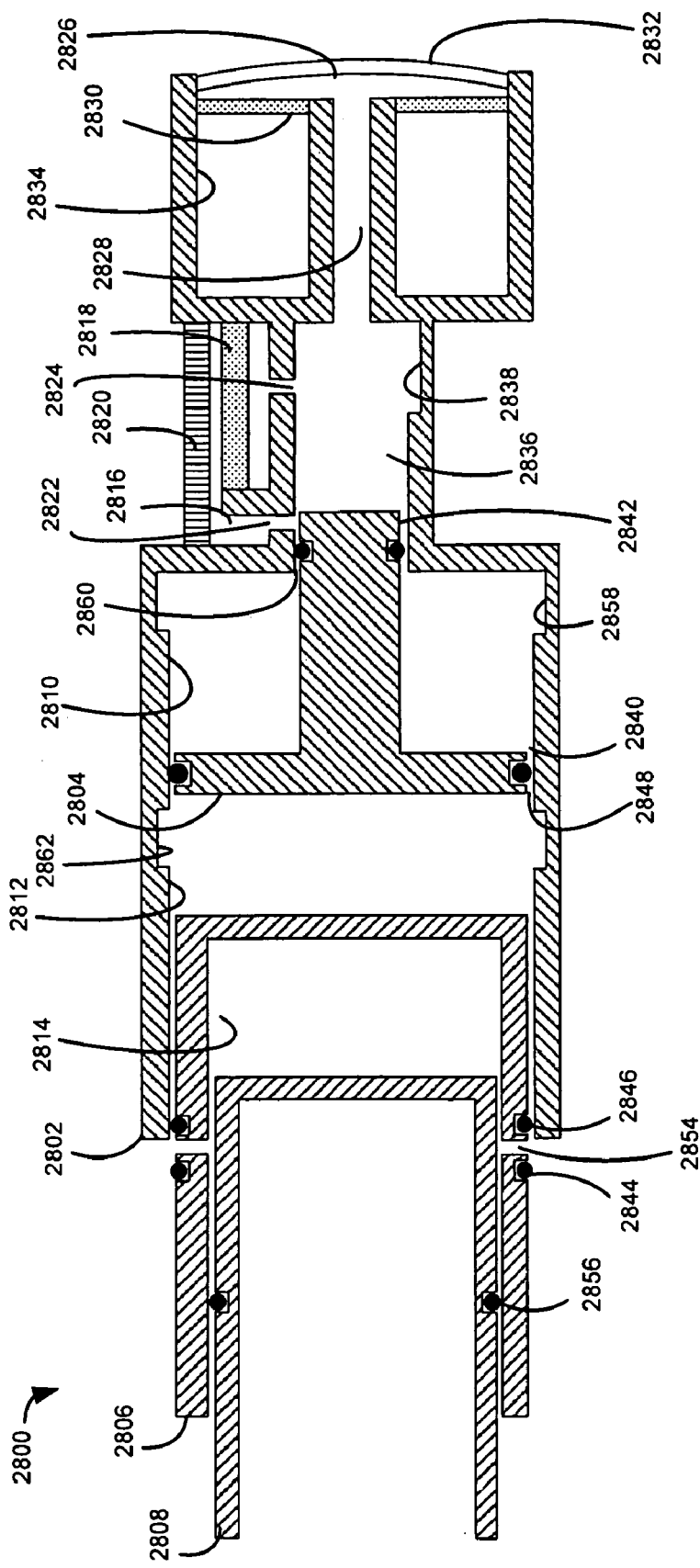
FIG. 29 is another cross-sectional block diagram of assay system 2800.

FIG. 29 is a cross-sectional block diagram of assay system 2800, wherein the fluid controller system, including fluid controllers 2804, 2806, and 2808, is illustrated in corresponding initial or functionally closed positions. When fluid controllers 2804, 2806, and 2808 are in the initial positions, O-ring 2842 is sealingly engaged against an inner surface of housing portion 2802, between first fluid chamber outlet 2860 and sample chamber inlet 2822, to substantially preclude fluid flow from fluid chamber 2810. Similarly, O-ring 2840 is sealingly engaged against an inner surface of housing portion 2802 to substantially preclude fluid flow from fluid chamber 2812 through second fluid chamber outlet 2848. O-rings 2844 and 2846 are sealingly engaged against an inner surface of housing portion 2802 to substantially preclude fluid flow from fluid chamber 2814 through third fluid chamber outlet 2854.

O-Rings 2840, 2842, 2844, 2846, and 2856 cause fluid controllers 2804, 2806, and 2808 to be pressurizably engaged with one another, such that a force applied to fluid controller 2808, in the direction of fluid controllers 2806 and 2804, causes the fluid controller system to serially move into functionally open positions with respect to first, second, and third fluid chambers 2810, 2812, and 2814, as described below with respect to FIGS. 30-33.

Figure 30:
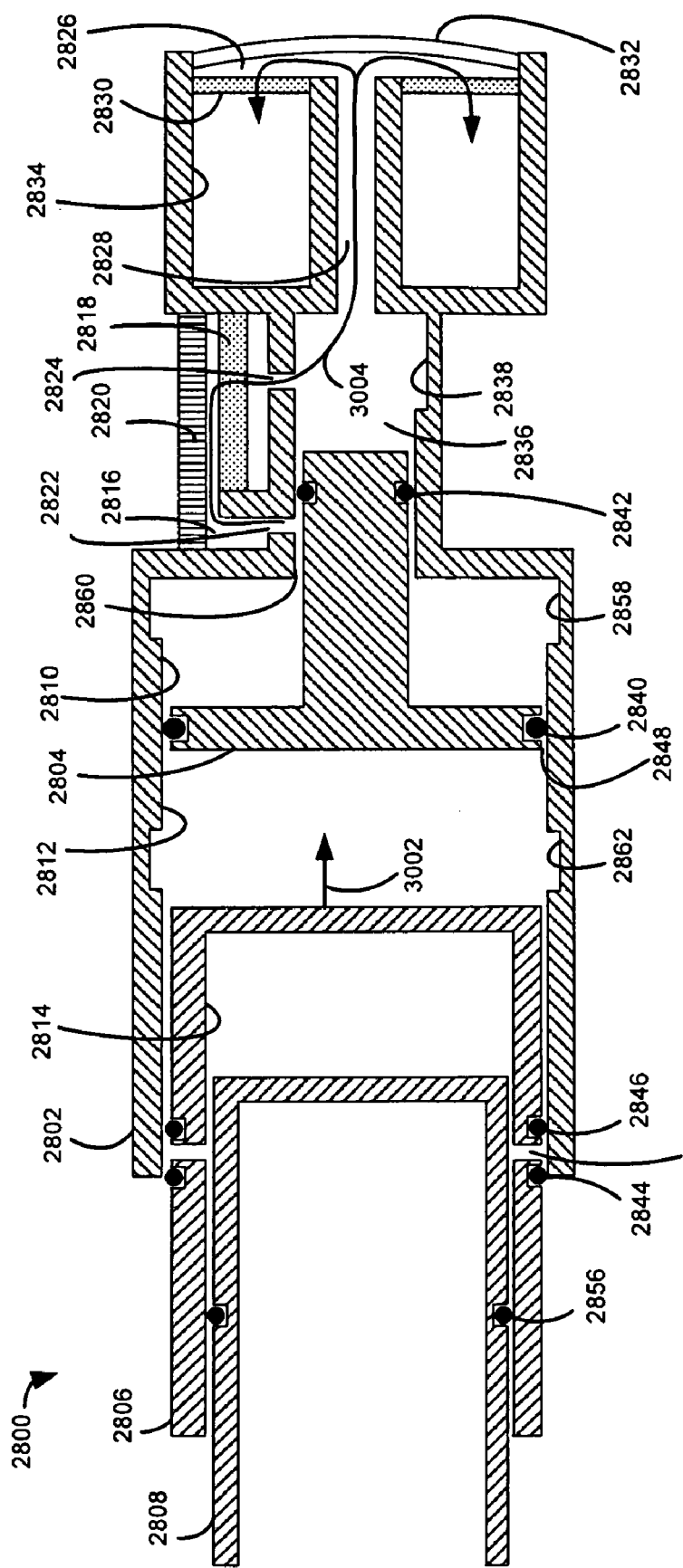
FIG. 30 is another cross-sectional block diagram of assay system 2800.

FIG. 30 is a cross-sectional block diagram of assay system 2800, wherein the fluid controller system has moved in a direction of arrow 3002, relative to housing portion 2802, to align first fluid chamber outlet 2860 with a fluid path 3004 to assay chamber 2826. This is referred to herein as a first functionally open position. Fluid path 3004 includes sample chamber inlet 2822, sample chamber 2816, sample chamber outlet 2824, transient fluid chamber 2836, and assay chamber inlet 2828.

As continued force is applied to fluid controller 2808, fluid controllers 2806 and 2808 continue to move in the direction of arrow 3002, to expel fluid from first fluid chamber 2810 to assay chamber 2826, through fluid path 2804. The fluid may flow over or through assay substrate 2830, to waste fluid chamber 2834.

Figure 31:
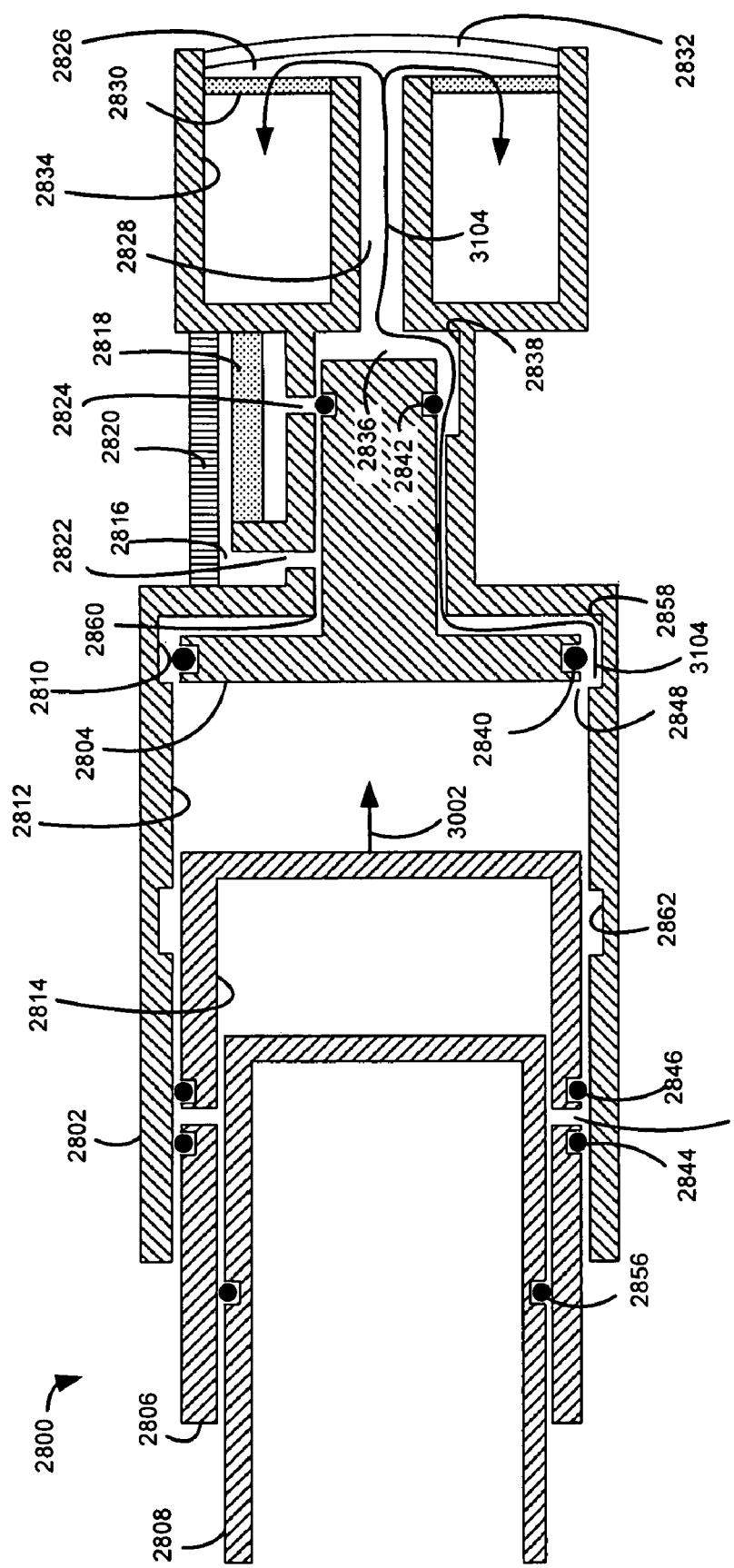
FIG. 31 is another cross-sectional block diagram of assay system 2800.

FIG. 31 is a cross-sectional block diagram of assay system 2800, wherein the fluid controller system has moved further in the direction of arrow 3002, to align second fluid chamber outlet 2848 with a fluid path 3104 to assay chamber 2826. This is referred to herein as a second functionally open position. Fluid path 3104 includes fluid channel 2858 to bypass O-ring 2840 and first fluid controller 2804, first fluid chamber outlet 2860, transient fluid chamber 2836, fluid channel 2838 to bypass O-ring 2842, and assay chamber inlet 2828.

As continued force is applied to fluid controller 2808, fluid controllers 2806 and 2808 continue to move in the direction of arrow 3002, to expel fluid from second fluid chamber 2812 to assay chamber 2826, through fluid path 3104. The fluid may flow over or through assay substrate 2830, to waste fluid chamber 2834.

Figure 32:
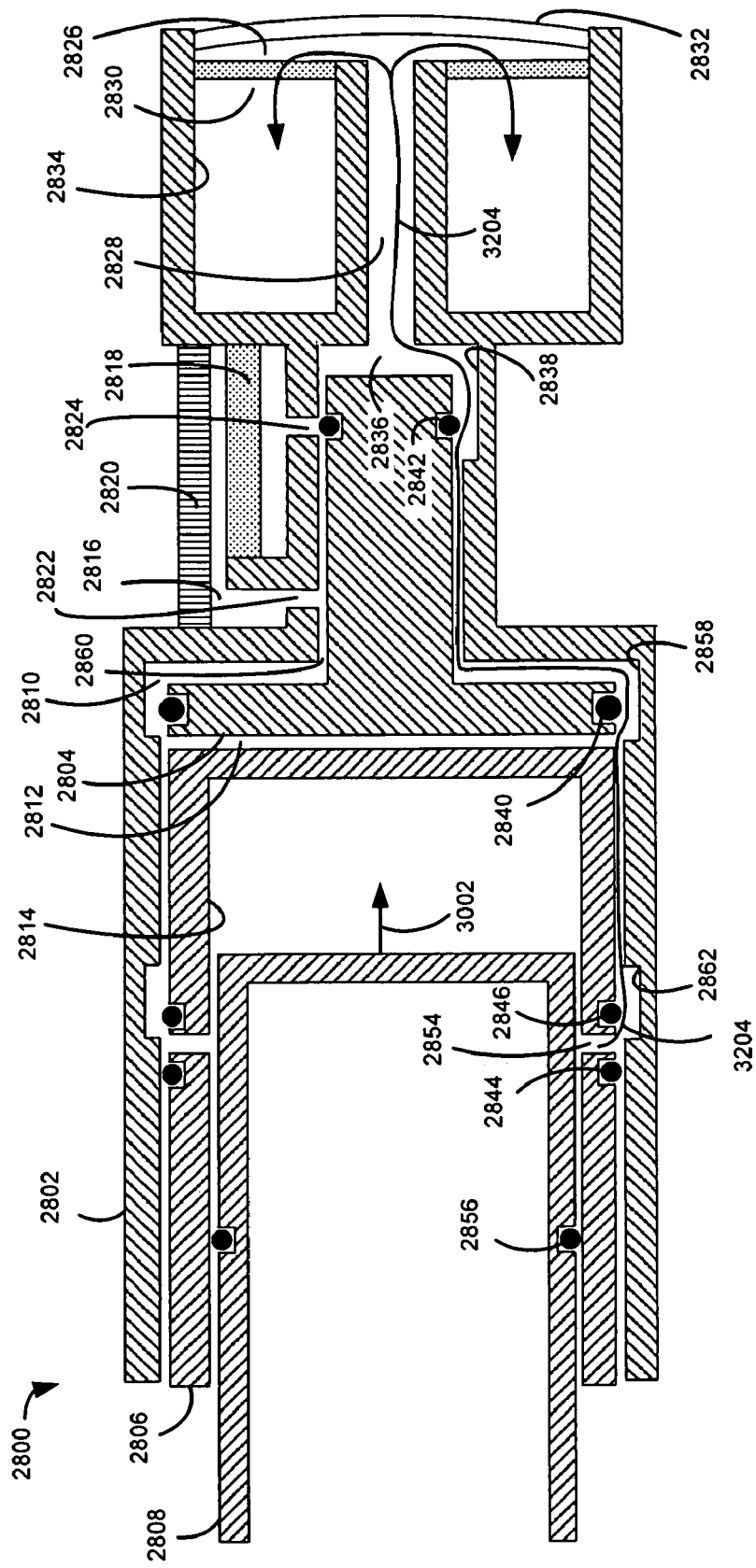
FIG. 32 is another cross-sectional block diagram of assay system 2800.

FIG. 32 is a cross-sectional block diagram of assay system 2800, wherein the fluid controller system has moved further in the direction of arrow 3002, to align third fluid chamber outlet 2848 with a fluid path 3204 to assay chamber 2826. This is referred to herein as a third functionally open position. Fluid path 3204 includes fluid channel 2862 to bypass O-ring 2846 and second flow controller 2806, fluid channel 2858, first fluid chamber outlet 2860, transient fluid chamber 2836, and assay chamber inlet 2828.

As continued force is applied to fluid controller 2808, fluid controller 2808 continues to move in the direction of arrow 3002, to expel fluid from third fluid chamber 2814 to assay chamber 2826, through fluid path 3204. The fluid may flow over or through assay substrate 2830, to waste fluid chamber 2834.

Figure 33:
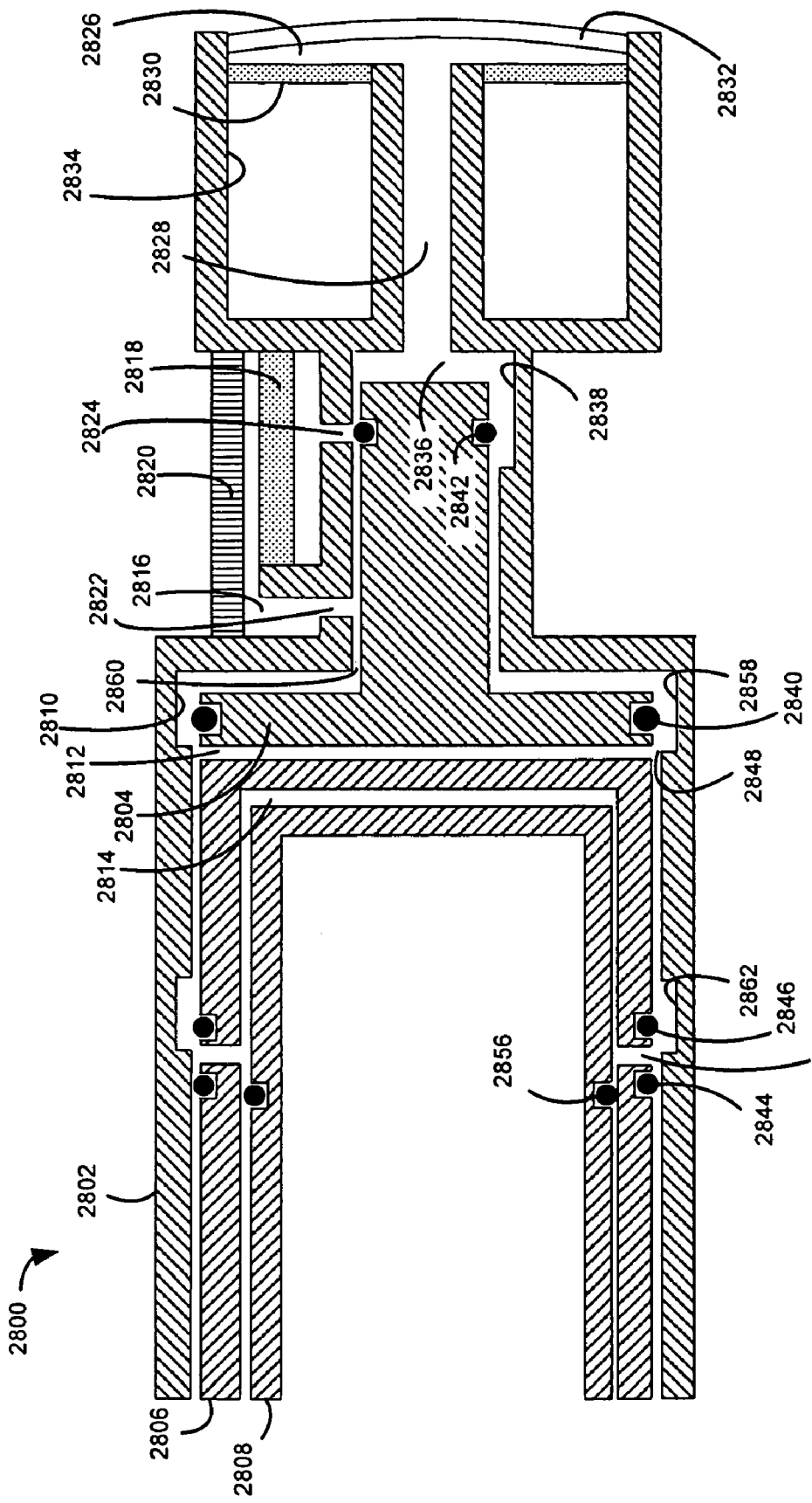
FIG. 33 is another cross-sectional block diagram of assay system 2800.

FIG. 33 is a cross-sectional block diagram of assay system 2800, wherein the fluid controller system has expelled fluid from third fluid chamber 2814.

Assay system 2800 may include an actuator system, which may be configured to act upon third fluid controller 2808.

One or more inlets, outlets, channels, and fluid pathways as described herein with respect to assay system 2200 and assay system 2800 may be implemented as one or more of gates and passageways as described in one or more preceding examples, an may include one or more of:
- a fluid channel within an inner surface of a housing;
- a fluid passage within a housing, having a plurality of openings through an inner surface of the housing;
- the fluid passage through a fluid controller; and
- a fluid channel formed within an outer surface of one of the fluid controllers.

One or more inlets, outlets, channels, fluid paths, gates, and passageways, as described herein, may include one or more flow restrictors, such as check valves, which may include a frangible check valve, to inhibit fluid flow when a pressure difference across the flow restrictor valve is below a threshold.

7. Exemplary Actuator Systems

A user-initiated actuator system may include one or more of a mechanical actuator, an electrical actuator, an electromechanical actuator, and a chemical reaction initiated actuator. Exemplary user-initiated actuator systems are disclosed below, one or more of which may be implemented with exemplary pumps disclosed above.

Figure 34:
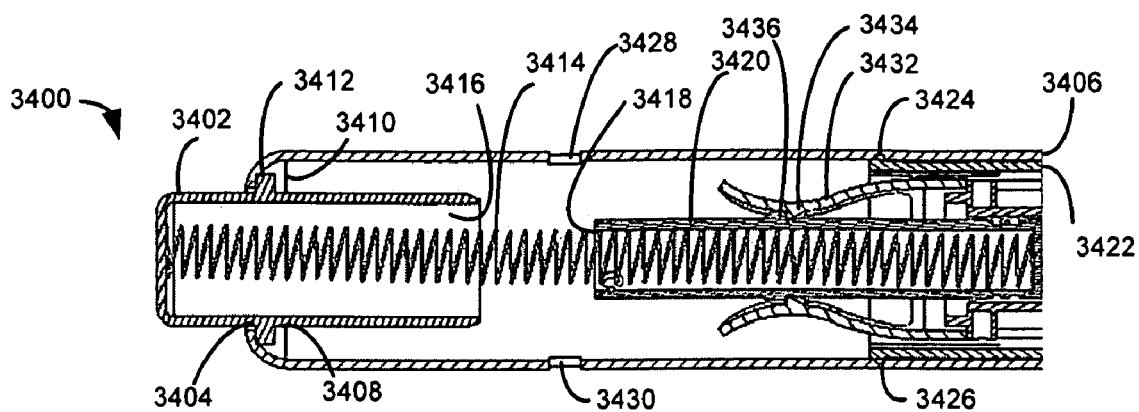
FIG. 34 is cross-sectional view of an exemplary mechanical actuator system 3400.

FIG. 34 is cross-sectional view of an exemplary mechanical actuator system 3400. Actuator system 3400 includes a button 3402 slideably disposed through an opening 3404 of an outer housing portion 3406, and through an opening 3408 of a frangible inner wall 3410 of outer housing portion 3406. Button 3402 includes a detent 3412 that extends beyond openings 3404 and 3408 to secure button 3402 between housing portion 3406 and frangible inner wall 3410.

Actuator system 3400 includes a compressible spring 3414 having a first end positioned within a cavity 3416 of button 3402, and a second end disposed within a cavity 3418 of a member 3420. Member 3420 may be coupled to, or may be a part of a fluid controller system, such a part of a plunger or fluid controller as described and illustrated in one or more examples herein.

Actuator system 3400 includes an inner housing portion 3422, slideably engaged within outer housing portion 3406. Inner housing portion 3422 includes one or more detents, illustrated here as detents 3424 and 3426, to lockingly engage one or more corresponding openings 3428 and 3430 in an inner surface of outer housing portion 3402, as described below with respect to FIG. 35.

Actuator system 3400 includes one or more frangible snaps 3432 coupled, directly or indirectly, to inner housing portion 3422. Frangible snap 3432 includes a locking detent 3434, and member 3420 includes a corresponding locking detent 3436 to releasably couple member 3420 to frangible snap 3432.

Operation of actuator system 3400 is described below with respect to FIGS. 35 and 36.

Figure 35:
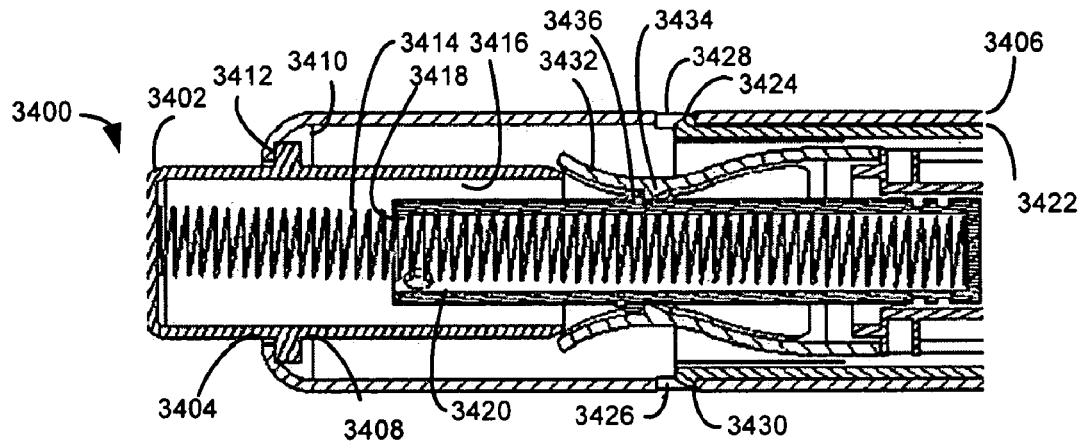
FIG. 35 is another cross-sectional view of mechanical actuator system 3400.

FIG. 35 is cross-sectional view of actuator system 3400, wherein inner housing detents 3424 and 3426 are lockingly engaged with outer housing openings 3428 and 3430. This configuration may be achieved by sliding or compressing inner housing portion 3422 and outer portion 3406 towards one another. In the configuration of FIG. 35, spring 3414 is in a compressed position, and has potential energy to cause a fluid controller system associated with member 3420 to move as described in examples above. In this configuration, button 3402 is proximate to frangible snap 3432, while frangible snap detent 3434 and member locking detent 3436 remain engaged with one another to preclude member 3420 from moving in response to the potential energy of compressed spring 3414. Inner housing detents 3424 and 3426 remain lockingly engaged with outer housing openings 3428 and 3430 to preclude inner housing portion 3422 and outer housing portion 3406 from moving apart from one another in response to the potential energy of compressed spring 3414.

Figure 36:
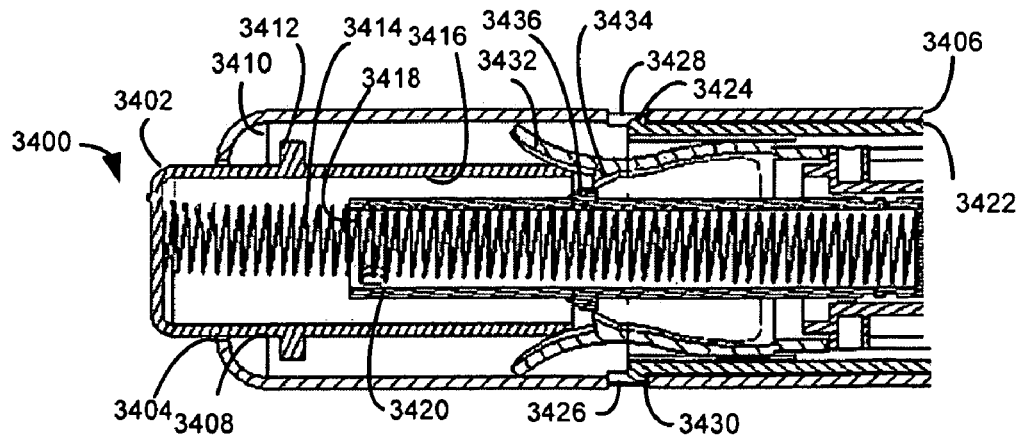
FIG. 36 is another cross-sectional view of mechanical actuator system 3400.

FIG. 36 is cross-sectional view of exemplary actuator system 3400, wherein button 3402 is pressed with sufficient force to move detent 3412 past frangible wall 3408, and to cause button 3402 to spread frangible snap 3432. Upon spreading of frangible snap 3432, frangible snap detent 3434 and member locking detent 3436 disengage from one another, to allow the potential force of compressed spring 3424 to act on member 3420.

Actuator system 3400 may be implemented within assay system 300 in FIG. 3, as described below with respect to FIGS. 37 and 38.

Figure 37:
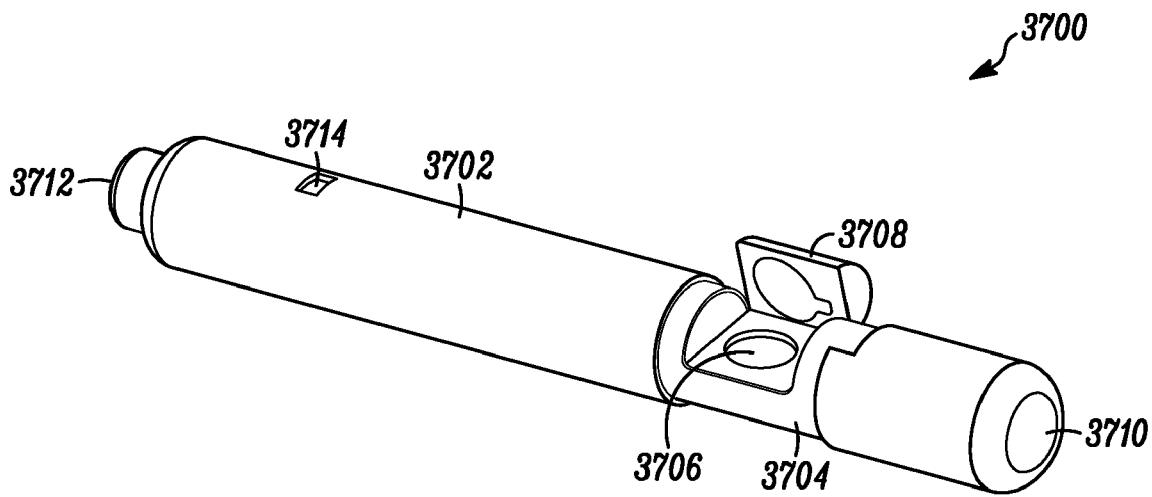
FIG. 37 is a perspective view of an exemplary assay system 3700.

FIG. 37 is a perspective view of an exemplary assay system 3700, including an outer housing portion 3702 and an inner housing portion 3704, illustrated here in a first position relative to one another. Outer housing portion 3702 may correspond to outer housing portion 3406 (FIGS. 34-36), and inner housing portion 3704 may correspond to inner housing portion 3422. Assay system 3700 further includes an actuator button 3712 and an opening 3714, which may correspond to button 3402 and opening 3428, respectively, in FIGS. 34-36.

Figure 38:
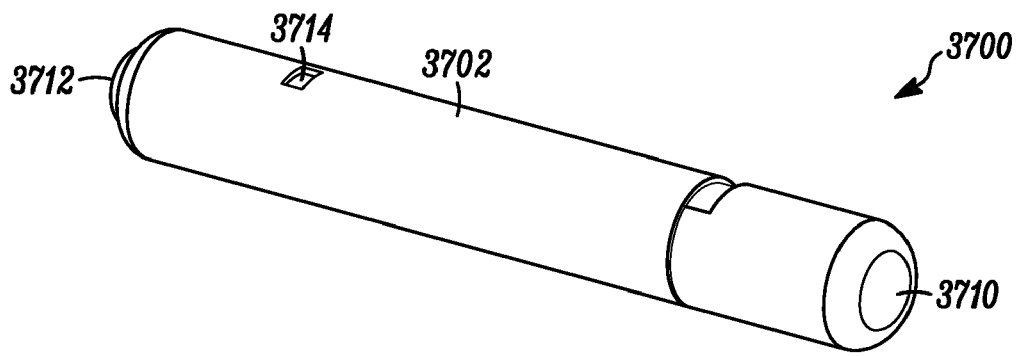
FIG. 38 is another perspective view of assay system 3700.

FIG. 38 is another perspective view of assay system 3700, wherein outer housing portion 3702 and inner housing portion 3704 are illustrated in a second position relative to one another, which may correspond to FIG. 35 or 36.

Assay system 3700 further includes a sample chamber 3706, a sample chamber lid hingedly connected to inner housing portion 3704 to enclose and seal sample chamber 3706, and a display window 3710.

Assay system 3700 may include assay system 2200 (FIGS. 22-27), wherein inner housing portion 3704 correlates to housing portion 2202, sample chamber 3706 correlates to sample chamber 2216, and display window 3710 correlates to display window 2232.

Similarly, assay system 3700 may include assay system 2800 (FIGS. 28-33), wherein inner housing portion 3704 correlates to housing portion 2802, sample chamber 3706 correlates to sample chamber 2816, and display window 3710 correlates to display window 2832.

Similarly, assay system 3700 may include one or more pumps 600, 900, 1100, 1500, 1800, 2100.

Figure 39:
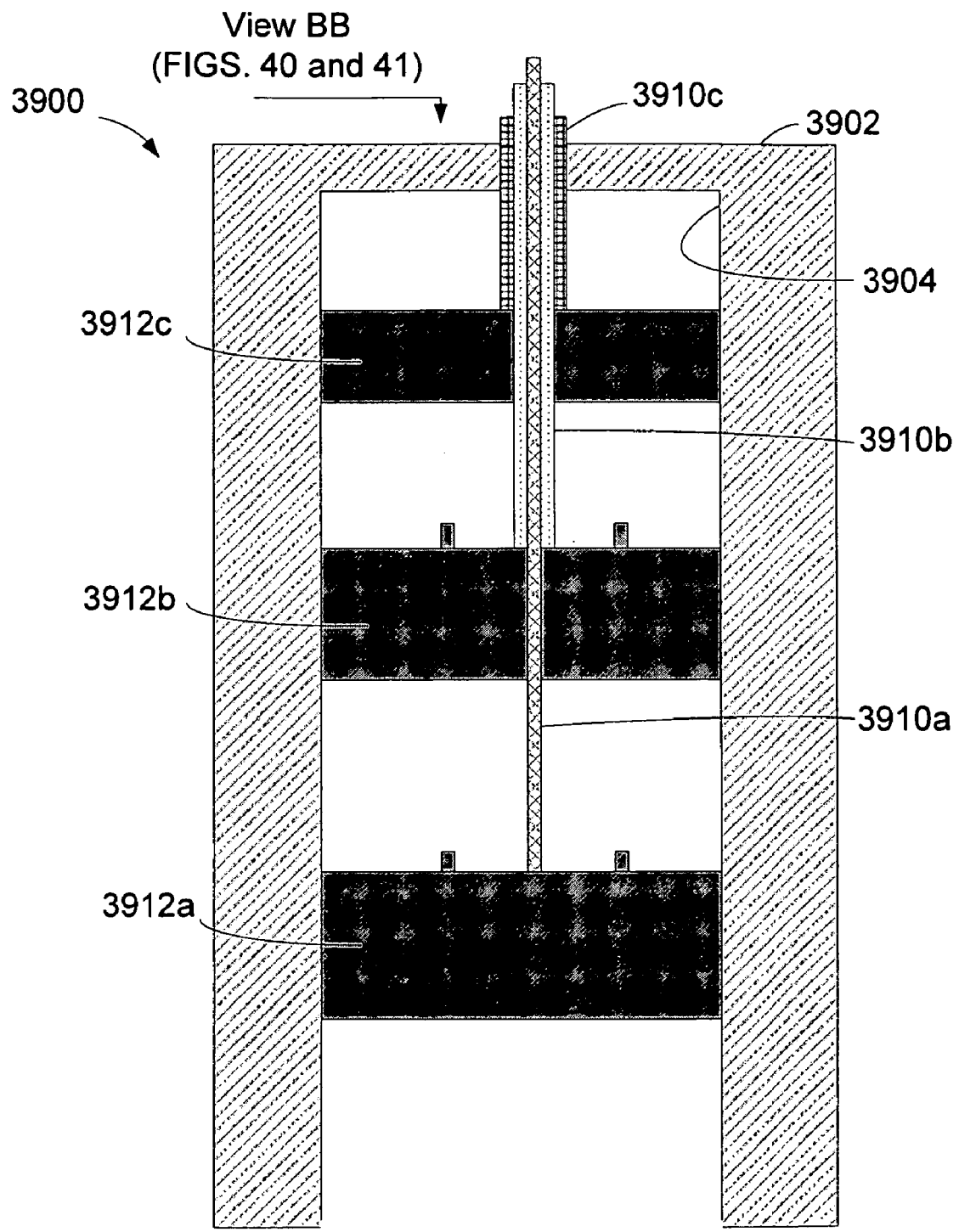
FIG. 39 is a cross-sectional diagram of exemplary mechanical control rod actuators 3910.

A user-initiated actuator may be configured to individually control multiple sets of one or more plungers or fluid controllers. FIG. 39 is a cross-sectional diagram of a portion of an exemplary assay system 3900, including a plurality of control rods, or stems 3910a-3910c, to individually control, through pushing and/or pulling, a plurality of sets of one or more plungers or fluid controllers, in response to corresponding forces from a user-initiated actuator.

One or more stems 3910 may be coupled to a plurality of adjacent and/or non-adjacent plungers. Stems 3910 may be individually controllable to exert a force, push and/or pull, on respective plungers.

Figure 40:
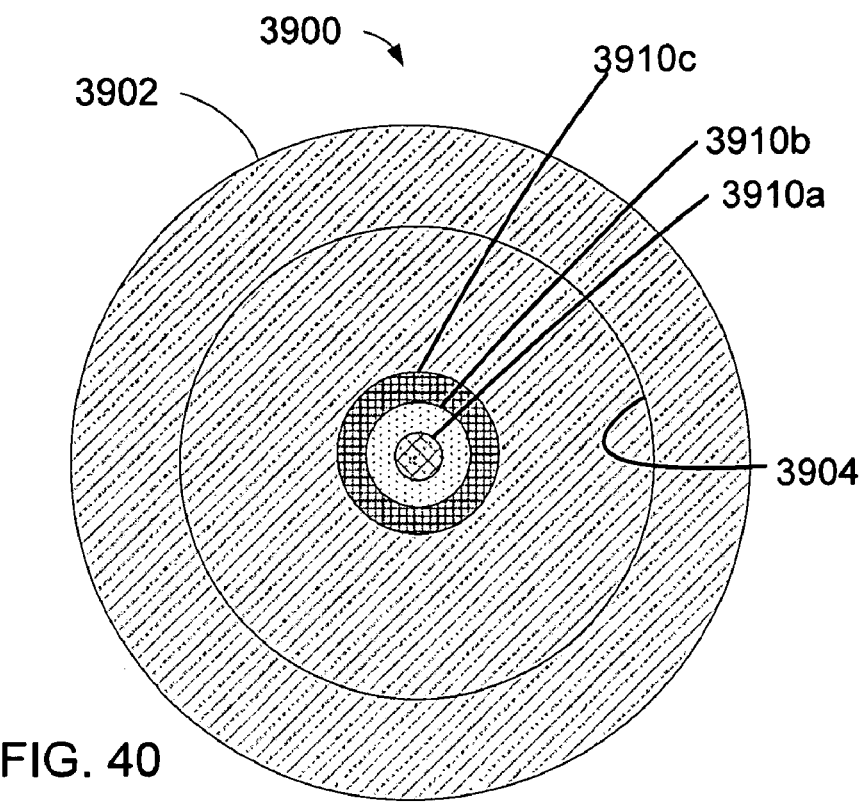
FIG. 40 is another cross-sectional diagram of control rod actuators 3910.
Figure 41:
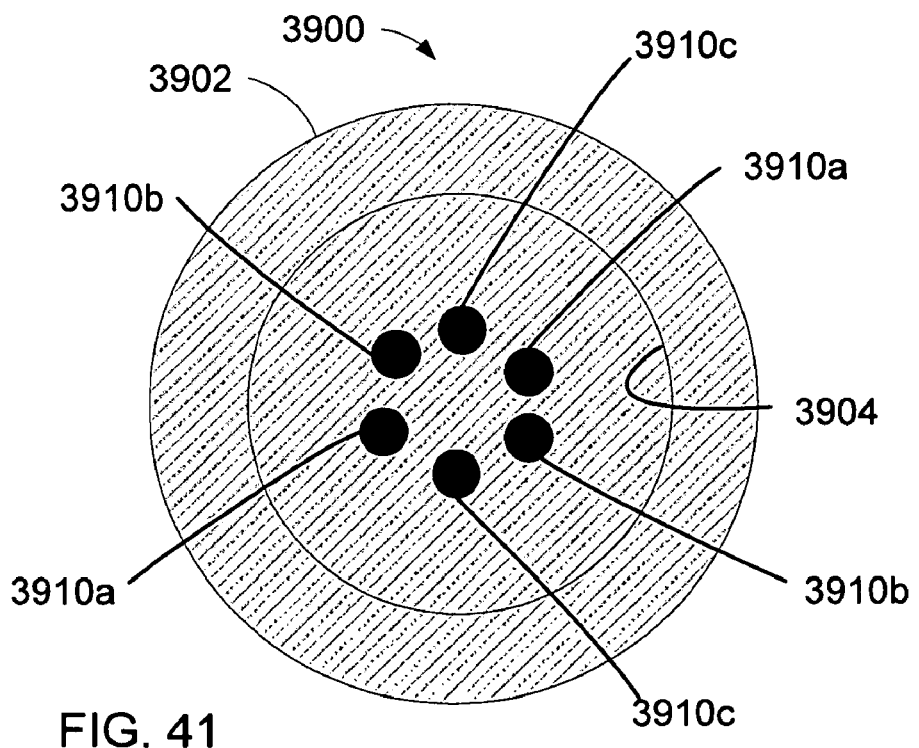
FIG. 41 is another cross-sectional diagram of control rod actuators 3910.

One or more of stems 3910 may be telescoped inside another one of stems 3910, as illustrated in FIG. 40. One or more of stems 3910 may be implemented as individual stems 3910, as illustrated in FIG. 41.

Figure 21:
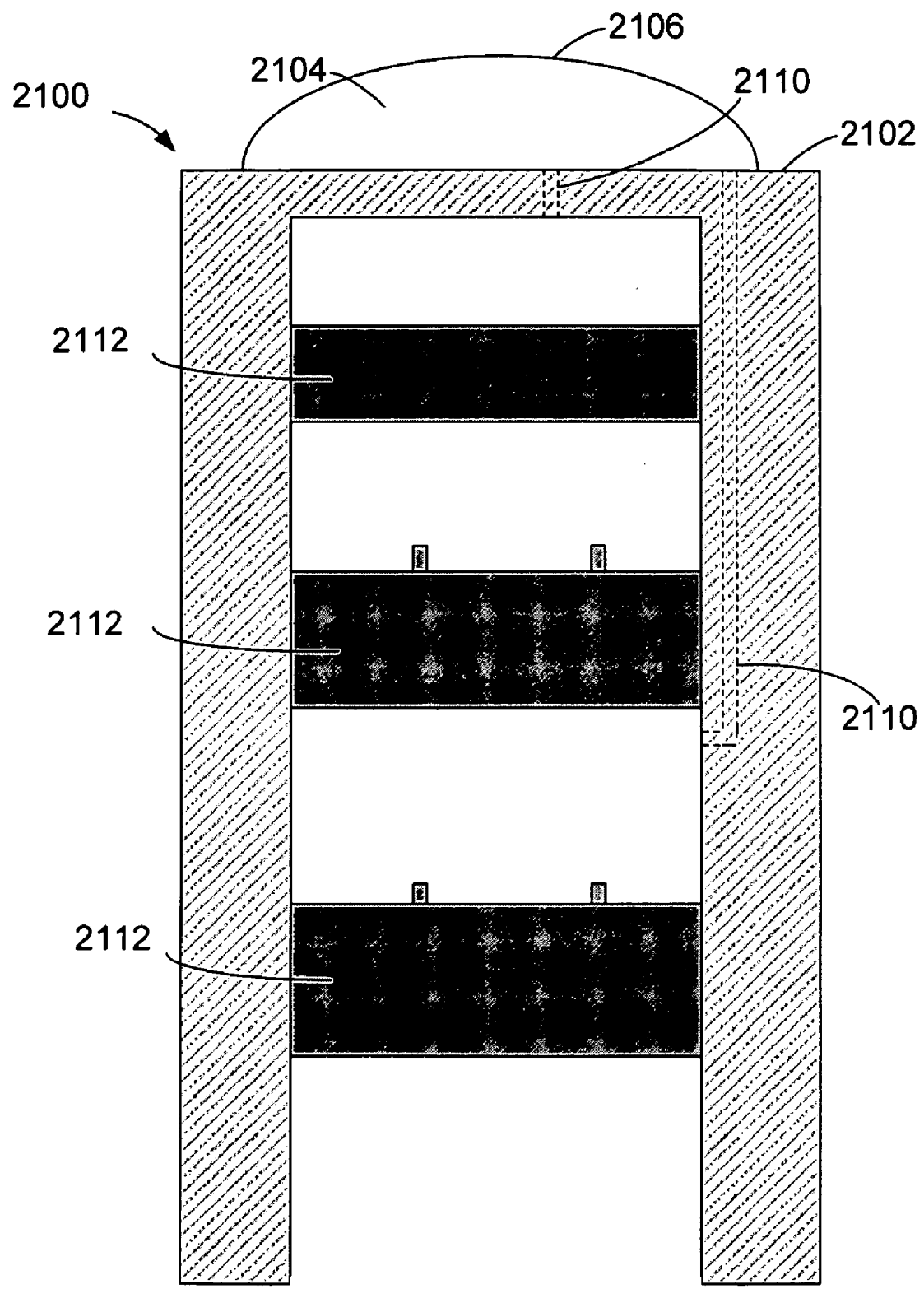
FIG. 21 is a cross-sectional block diagram of a portion of an assay system 2100, including a user-initiated actuator.

FIG. 21 is a cross-sectional block diagram of a portion of an assay system 2100, including a user-initiated actuator 2104, and one or more fluid passages 2110 within a housing 2102, between user-initiated actuator 2104 and one or more fluid chambers. User-initiated actuator 2104 may include a combination of chemicals, separated by a user-rupturable membrane, within a flexible tear-resistant membrane 2106, which, when combined, create a pressurized fluid, as is well known. The pressurized fluid may be gas or liquid. The pressurized fluid causes fluid controllers 2112 to move as described in one or more examples above. Multiple user-rupturable membranes may be implemented for multiple fluid passages 2110.

What is claimed is:

1. A portable, point-of-care assay system, comprising:
   a portable housing having a sample portion, an assay portion, a sample fluid passage between a fluid outlet of the sample portion and a fluid inlet of the assay portion, and a plurality of fluid chambers, each of the plurality of fluid chambers having a fluid chamber outlet;
   a fluid controller system separating the plurality of fluid chambers and movably disposed within the housing to align each of the plurality of fluid chamber outlets with a corresponding fluid path to one or more of another one of the fluid chambers, the sample portion, and the assay portion; and
   a user-initiated mechanical actuator coupled to the fluid controller system.

2. The system of claim 1, wherein one or more of the fluid paths include one or more of:
   a fluid channel within an inner surface of the housing;
   a fluid passage through a fluid controller within the fluid controller system; and
   a fluid channel formed within an outer surface of the fluid controller.

3. The system of claim 1, wherein the fluid controller system is configured to serially align the plurality of fluid chamber outlets with the corresponding fluid paths.

4. The system of claim 1, wherein the fluid controller system is configured to mix first and second fluids from corresponding first and second fluid chambers in a third fluid chamber, and move the mixed first and second fluids from the third fluid chamber to one or more of the sample portion and the assay portion.

5. The system of claim 1, wherein the fluid controller system includes a plurality of fluid controllers, wherein the fluid chambers are defined at least in part by the plurality of fluid controllers, and wherein the plurality of fluid controllers are configured to position the fluid chambers with respect to the fluid paths.

6. The system of claim 1, wherein the housing includes a waste fluid chamber and wherein the fluid controller system is configured to align at least one of the fluid chamber outlets with a fluid path to the assay portion and from the assay portion to the waste fluid chamber.

7. The system of claim 6, wherein the fluid controller system is configured to retain at least one fluid in the assay portion.

8. The system of claim 1, wherein the fluid controller system comprises a plurality of fluid controllers individually movably disposed within the housing.

9. The system of claim 1, wherein the user-initiated mechanical actuator is configured to pressurize the plurality of fluid chambers.

10. The system of claim 1, wherein the user-initiated mechanical actuator comprises a compressed-spring actuator.

11. The system of claim 10, wherein the user-initiated mechanical actuator further comprises:
a button disposed through a surface of the housing;
a spring coupled to the fluid controller system;
a releasable lock to releasably secure the spring and including a release tab aligned with the button.

12. The system of claim 11, wherein the housing includes:
first and second housing portions, wherein the second housing portion is longitudinally slideably movable within the first housing portion between a first relative position and a second relative position; and
a housing lock to couple the first and second housing portions to one another in the second relative position;
wherein the spring has a substantially uncompressed position corresponding to the first relative position and a substantially compressed position corresponding to the second relative position.

13. The system of claim 1, further comprising:
a diluent fluid solution disposed within a first one of the fluid chambers;
a labeled secondary binding pair molecule solution disposed within a second one of the fluid chambers; and
a wash solution disposed within a third one of the fluid chambers.

14. The system of claim 13, wherein the fluid controller system is configured to serially dispense the diluent fluid to the sample portion and to the assay portion, and the labeled secondary binding pair molecule solution and the wash solution to the assay portion without passing through the sample portion.

15. The system of claim 1, further comprising a light-transmissive window disposed over an opening in a surface of the housing to the assay chamber.

16. The system of claim 1, wherein the fluid controller system includes first and second fluid controllers, wherein the first fluid controller is positioned at least partially within the second fluid controller, and wherein an inner surface of the first fluid controller and an outer surface of the second fluid controller defines one of the fluid chambers.

17. The system of claim 1, wherein the fluid controller system is configured to serially open the fluid paths between at least a subset of the plurality of fluid chambers and one or more of the sample portion and the assay portion.

18. The system of claim 1, wherein the fluid controller system is implemented to force fluid from at least one of the fluid chambers, through the sample portion and the sample fluid passage, and into the assay portion, to move at least a portion of a sample from the sample portion to the assay portion.

* * * * *

UNITED STATES PATENT AND TRADEMARK OFFICE
CERTIFICATE OF CORRECTION

PATENT NO.        : 8,021,873 B2
APPLICATION NO.   : 12/228081
DATED             : September 20, 2011
INVENTOR(S)       : Brandon T. Johnson et al.

It is certified that error appears in the above-identified patent and that said Letters Patent is hereby corrected as shown below:

On the Title Page, Item (56), under "OTHER PUBLICATIONS", in column 2, line 1, After "Opinion" insert -- received --.

In the Drawings

Sheet 1 of 33, Box No. 104, FIG. 1, line 1, delete "Acutator" and insert -- Actuator --, therefor.

Sheet 2 of 33, Box No. 404, FIG. 4, line 1, delete "Dilutent" and insert -- Diluent --, therefor.

Sheet 2 of 33, Box No. 504, FIG. 5, line 1, delete "Acutator" and insert -- Actuator --, therefor.

Sheet 2 of 33, Box No. 506, FIG. 5, line 1, delete "Dilutent" and insert -- Diluent --, therefor.

In the Specifications

In column 4, line 43, delete "dilutent" and insert -- diluent --, therefor.

In column 5, line 3, delete "dilutent" and insert -- diluent --, therefor.

In column 5, line 7, delete "dilutent" and insert -- diluent --, therefor.

In column 5, line 44, delete "dilutent" and insert -- diluent --, therefor.

In column 5, line 45, delete "dilutent" and insert -- diluent --, therefor.

In column 6, line 27, delete "system" and insert -- system. --, therefor.

Signed and Sealed this
Fifteenth Day of April, 2014

Michelle K. Lee
*Deputy Director of the United States Patent and Trademark Office*

CERTIFICATE OF CORRECTION (continued)
U.S. Pat. No. 8,021,873 B2

In column 7, line 29, delete "dilutent" and insert -- diluent --, therefor.

In column 7, line 36, delete "dilutent" and insert -- diluent --, therefor.

In column 7, line 50, delete "dilutent" and insert -- diluent --, therefor.

In column 7, line 53, delete "dilutent" and insert -- diluent --, therefor.

In column 7, line 55, delete "dilutent" and insert -- diluent --, therefor.

In column 7, line 65, delete "chamber," and insert -- chamber. --, therefor.

In column 8, line 2-3, delete "Corporatation," and insert -- Corporation, --, therefor.

In column 11, line 32, delete "outlet, The" and insert -- outlet. The --, therefor.

In column 16, line 55-56, delete "electromechanical" and insert -- electro-mechanical --, therefor.

In the Claims

In column 18, line 53, in claim 1, delete "of another" and insert -- of, another --, therefor.